US011702470B2

(12) United States Patent
Di Giovanni et al.

(10) Patent No.: US 11,702,470 B2
(45) Date of Patent: Jul. 18, 2023

(54) USE OF CXCL13 BINDING MOLECULES TO PROMOTE PERIPHERAL NERVE REGENERATION

(71) Applicant: IMPERIAL COLLEGE INNOVATIONS LIMITED, London (GB)

(72) Inventors: Simone Di Giovanni, London (GB); Luming Zhou, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 0 days.

(21) Appl. No.: 17/341,546

(22) Filed: Jun. 8, 2021

(65) Prior Publication Data
US 2021/0388075 A1     Dec. 16, 2021

Related U.S. Application Data

(60) Provisional application No. 63/037,755, filed on Jun. 11, 2020.

(51) Int. Cl.
*C07K 16/24*     (2006.01)
*A61P 25/28*     (2006.01)
*A61K 39/00*     (2006.01)

(52) U.S. Cl.
CPC ............. *C07K 16/24* (2013.01); *A61P 25/28* (2018.01); *A61K 2039/505* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,225,539 A | 7/1993 | Winter |
| 5,585,089 A | 12/1996 | Queen et al. |
| 5,693,761 A | 12/1997 | Queen et al. |
| 5,693,762 A | 12/1997 | Queen et al. |
| 5,859,205 A | 1/1999 | Adair et al. |
| 5,892,019 A | 4/1999 | Schlom et al. |
| 5,939,598 A | 8/1999 | Kucherlapati et al. |
| 6,180,370 B1 | 1/2001 | Queen et al. |
| 9,963,504 B2 | 5/2018 | Klimatcheva et al. |
| 2002/0102208 A1 | 8/2002 | Chinn et al. |
| 2008/0199481 A1 | 8/2008 | Barker et al. |
| 2008/0227704 A1* | 9/2008 | Kamens .................. A61P 43/00 435/69.6 |
| 2014/0147447 A1* | 5/2014 | Klimatcheva ........... A61P 29/00 536/23.53 |

FOREIGN PATENT DOCUMENTS

| | | |
|---|---|---|
| WO | 0127160 A1 | 4/2001 |
| WO | 2012031099 A2 | 3/2012 |
| WO | 2020057540 A1 | 3/2020 |

OTHER PUBLICATIONS

Kussie "A Single Engineered Amino Acid Substitution Changes Antibody Fine Specificity" J immunol 152(1):146-52 (Year: 1994).*
Biocompare "mab5261 antibody products" and "mab5378 antibody products" accessed from biocompare.com on Jul. 25, 2022 (Year: 2022).*
Jiang "CXCL13 drives spinal astrocyte activation and neuropathic pain via CXCR5" JCI 126(2):745-761 (Year: 2016).*
Trolese "CXCL13/CXCR5 signalling is pivotal to preserve motor neurons in amyotrophic lateral sclerosis" Ebiomed 62 (Year: 2020).*
Gong et al., "Importance of Cellular Microenvironment and Circulatory Dynamics in B Cell Immunotherapy", J. Immunol., vol. 174: 817-826, 2005.
Hamaguchi et al., "The Peritoneal Cavity Provides a Protective Niche for B1 and Conventional B Lymphocytes during Anti-CD20 Immunotherapy in Mice", J. Immunol., vol. 174:4389-4399, 2005.
Gunther et al., "Prediction of lymph node metastasis in colorectal carcinoma by expression of chemokine receptor CCR7", Int. J. Cancer, vol. 116:726-733, 2005.
Meijer et al.,"The CXCR5 Chemokine Receptor Is Expressed by Carcinoma Cells and Promotes Growth of Colon Carcinoma in the Liver", Cancer Res., vol. 66: 9576-9582, 2006.
Panse et al., "Chemokine CXCL13 is overexpressed in the tumour tissue and in the peripheral blood of breast cancer patients", British Journal of Cancer, vol. 99:930-938, 2008.
Burkle et al., "Overexpression of the CXCR5 chemokine receptor, and its ligand, CXCL13 in B-cell chronic lymphocytic leukemia", Blood 110:3316-3325, 2007.
Singh et al., "Serum CXCL13 positively correlates with prostatic disease, prostate-specific antigen and mediates prostate cancer cell invasion, integrin clustering and cell adhesion", Cancer Letters, vol. 283 (1):29-35, 2009.
Lorei et al., "Peripheral Nerve Injuries in Athletes", Sports Medicine, vol. 16 (2): 130-47, 1993. Abstract.
Remington et al., "Remington's Pharmaceutical Sciences", MackPublishing Co., 16th ed., 1980. Abstract.
Jalkanen, et al., "Heparan Sulfate Proteoglycans from Mouse Mammary Epithelial Cells: Localization on the Cell Surface with a Monoclonal Antibody", J. Cell. Biol., vol. 101:976-985, 1985.
Jalkanen et al., "Cell surface proteoglycan of mouse mammary epithelial cells is shed by cleavage of its matrix-binding ectodomain from its membrane-associated domain", J. Cell Biol., vol. 105:3087-3096, 1987.
Huang et al., "Systematic and integrative analysis of large gene lists using DAVID Bioinformatics Resources", Nature Protoc., vol. 4(1):44-57, 2009. Abstract.

(Continued)

*Primary Examiner* — Adam Weidner
(74) *Attorney, Agent, or Firm* — KDW Firm PLLC

(57) ABSTRACT

Provided herein are methods for promoting axonal regeneration of sensory neurons and functional recovery of neurons following peripheral nerve injury in a subject experiencing aging-dependent nerve regenerative decline, the method comprising administering to a subject in need thereof an effective amount of an isolated binding molecule which specifically binds to CXCL13.

17 Claims, 10 Drawing Sheets

Figure 1A:
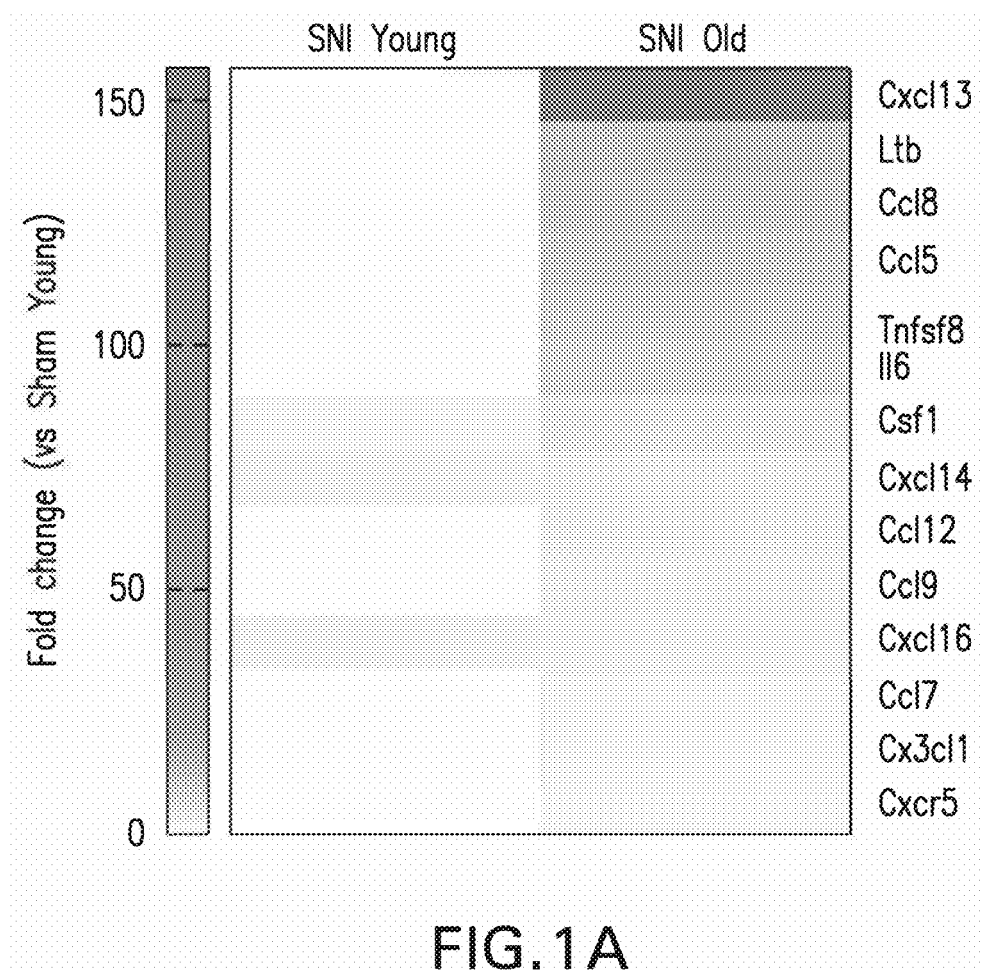

Specification includes a Sequence Listing.

(56) References Cited

OTHER PUBLICATIONS

Huang et al., "Bioinformatics enrichment tools: paths toward the comprehensive functional analysis of large gene lists", Nucleic Acids Res., vol. 37(1): 1-13, 2009.
Hulsen et al., "BioVenn—a web application for the comparison and visualization of biological lists using area-proportional Venn diagrams", BMC Genomics, vol. 9(1):488, 2008.
Shannon et al., "Cytoscape: a software environment for integrated models of biomolecular interaction networks", Genome Research, vol. 13(11):2498-504, Nov. 2003.
Chen et al., "Presynaptic GABAergic inhibition regulated by BDNF contributes to neuropathic pain induction", Nature Communications, vol. 5, 5331, 2014.
Hargreaves et al., "A new and sensitive method for measuring thermal nociception in cutaneous hyperalgesia", Pain, vol. 32, 77-88, 1988. Abstract.
Zinkernagel, "On cross-priming of MHC class I-specific CTL: rule or exception?", European Journal of Immunology, vol. 32, 2385-2392, 2002.
Zaldumbide et al., "A potentially immunologically inert derivative of the reverse tetracycline-controlled transactivator", Biotechnology Letters, vol. 32, 749-754, 2008.
Burnside et al., "Immune-evasive gene switch enables regulated delivery of chondroitinase after spinal cord injury", Brain, vol. 141, 2362-2381, 2018.
Hoyng et al., "Developing a potentially immunologically inert tetracycline-regulatable viral vector for gene therapy in the peripheral nerve", Gene Therapy 21, 549-557, 2014.
DeVivo, M.J., and Chen, Y, "Trends in New Injuries, Prevalent Cases, and Aging With Spinal Cord Injury", Archives of Physical Medicine and Rehabilitation, vol. 92, pp. 332-338, Mar. 2011.
Singh et al., "Global Prevalence and Incidence of Traumatic Spinal Cord Injury", Clinical Epidemiology, vol. 6, pp. 309-331, 2014.
Nagano, A., "Treatment of Brachial Plexus Injury", Journal of Orthopaedic Science, vol. 3, Issue 1, pp. 71-80; Jan. 1998. Abstract.
Pestronk et al., "Effects of Aging on Nerve Sprouting and Regeneration", Experimental Neurology, vol. 70, Issue 1, 65-82; Oct. 1980. Abstract.
Tanaka and deF. Webster, "Myelinated Fiber Regeneration After Crush Injury is Retarded in Sciatic Nerves of Aging Mice", Journal of Comparative Neurology, vol. 308, pp. 180-187; Jun. 8, 1991. Abstract.
Vaughan, "Effects of Advancing Age on Peripheral Nerve Regeneration", Journal of Comparative Neurology, vol. 323, pp. 219-237, Sep. 8, 1992. Abstract.
Verdú et al., "Influence of Aging on Peripheral Nerve Function and Regeneration", Journal of the Peripheral Nervous System, vol. 5, 191-208, 2000.
Kang and Lichtman, "Motor Axon Regeneration and Muscle Reinnervation in Young Adult and Aged Animals", . Journal of Neuroscience, vol. 33, 19480-19491; 2013.
Painter et al., "Diminished Schwann Cell Repair Responses Underlie Age-Associated Impaired Axonal Regeneration", Neuron, vol. 83, 331-343, Jul. 16, 2014.
Geoffroy et al., "Evidence for an Age-Dependent Decline in Axon Regeneration in the Adult Mammalian Central Nervous System", Cell Reports, vol. 15, Issue 2, 238-246, Apr. 12, 2016.
Barzilai et al., "The Critical Role of Metabolic Pathways in Aging", Diabetes, vol. 61(6), 1315-1322; Jun. 2012.
Lardenoije et al., "The Epigenetics of Aging and Neurodegeneration", Progress in Neurobiology, vol. 131, 21-66, Aug. 2015.
Pomatto and Davies, "The Role of Declining Adaptive Homeostasis in Ageing", The Journal of Physiology, vol. 595 (24), 7275-7309, Oct. 13, 2017.
Taylor and Dillin, "Aging as an Event of Proteostasis Collapse", Cold Spring Harbor Perspectives in Biology 3, a004440, 17 pages, 2011.
Weiskopf et al., "The Aging of the Immune System", Transplant International, vol. 22, 1041-1050, Oct. 1, 2009.
Harlow et al., "Antibodies: A Laboratory Manual", 2nd ed.; Cold Spring Harbor Laboratory Press, 1988. Abstract.
Hamers-Casterman et al., "Naturally Occurring Antibodies Devoid of Light Chains", Nature, 363:446-448, Jun. 1993. Abstract.
Kabat et al., "Sequences of Proteins of Immunological Interest", U.S. Dept. of Health and Human Services, 1983. Abstract.
Chothia and Lesk, "Canonical Structures for the Hypervariable Regions of Immunoglobulins", Journal of Molecular Biology, 196:901-917, 1987.
Brochet et al., "IMGT/V-QUEST: the highly customized and Integrated System for IG and TR Standardized V-J and V-D-J Sequence Analysis", Nucleic Acids Research, vol. 36:W503-508, 2008.
Legler et al., "B Cell-Attracting Chemokine 1, a Human CXC Chemokine Expressed in Lymphoid Tissues, Selectively Attracts B Lymphocytes Via BLR1/CXCR5", J. Exp. Med. 187 (4): 655-60; Feb. 1998.
Ansel et al., "CXCL13 is Required for B1 Cell Homing, Natural Antibody Production, and Body Cavity Immunity", Immunity 16(1): 67-76, Jan. 2002.
Ansel et al. "A Chemokine-Driven Positive Feedback Loop Organizes Lymphoid Follicles", Nature. 406 (6793): 309-14, Jul. 2000. Abstract.
Jones et al., "Replacing the Complementarity-Determining Regions in a Human Antibody with Those from a Mouse", Nature 321:522-525, 1986.
Riechmann et al., "Reshaping human antibodies for therapy", Nature 332:323-327 and 323-329, 1988. Abstract.
Verhoeyen et al., "Reshaping Human Antibodies: Grafting an Antilysozyme Activity", Science 239:1534-1536, 1988. Abstract.
Presta, "Antibody Engineering", Current Opinion in Structural Biology, vol. 2(4):593-596, 1992. Abstract.
Gunn et al., "A B-Cell-Homing Chemokine Made in Lymphoid Follicles Activates Burkitt's Lymphoma Receptor-1", Nature, vol. 391 (6669):799-803, 1998. Abstract.
Fenrich K. et al, "Axonal Regeneration in the Peripheral and Central Nervous Systems—Current Issues and Advances", Can J Neurol Sci., vol. 31(2):142-56, May 2004.
Corcione et al., "Recapitulation of B Cell Differentiation in the Central Nervous System of Patients with Multiple Sclerosis", PNAS 101(30):11064-11069, 2004.
Serafini et al., "Detection of Ectopic B-cell Follicles with Germinal Centers in the Meninges of Patients with Secondary Progressive Multiple Sclerosis", Brain Pathol. 14:164-174, 2004. Abstract.
Magliozzi et al., "Meningeal B-cell Follicles in Secondary Progressive Multiple Sclerosis Associate with Early Onset of Disease and Severe Cortical Pathology", Brain, vol. 130: 1089-1104, 2007.
Rioja et al., "Potential novel biomarkers of disease activity in rheumatoid arthritis patients: CXCL13, CCL23, transforming growth factor α, tumor necrosis factor receptor superfamily member 9, and macrophage colony-stimulating factor", Arthritis & Rheumatism, vol. 58(8):2257-2267, 2008.
Shi et al., "Lymphoid Chemokine B Cell-Attracting Chemokine-1 (CXCL13) Is Expressed in Germinal Center of Ectopic Lymphoid Follicles Within the Synovium of Chronic Arthritis Patients", The Journal of Immunologists, vol. 166:650-655, 2001.
Schmutz et al., "Chemokine receptors in the rheumatoid synovium: upregulation of CXCR5", Arthritis Research and Therapy 7:R217-R229, 2005.
Hjelmstrom et al., "Lymphoid neogenesis: de novo formation of lymphoid tissue in chronic inflammation through expression of homing chemokines", J. Leukocyte Bio. 69:331-339, 2001.
Unkeless et al., "Structure and function of human and murine receptors for IgG", Ann. Rev. Immunol. 6:251-81, 1988. Abstract.
Nobutani et al., "Helicobacter heilmannii can induce gastric lymphoid follicles in mice via a Peyer's patch-independent pathway", FEMS Immunol Med Microbiol., vol. 60:156-164, 2010.
Steinmetz et al., "BCA-1/CXCL13 expression is associated with CXCR5-positive B-cell cluster formation in acute renal transplant rejection", Kidney International, vol. 67:1616-1621, 2005.
Barone et al., "CXCL13, CCL21, and CXCL12 Expression in Salivary Glands of Patients with Sjögren's Syndrome and MALT Lymphoma: Association with Reactive and Malignant Areas of Lymphoid Organization", J. Immuno. 180:5130-5140, 2008.

(56) References Cited

OTHER PUBLICATIONS

Lee et al., "Serum BLC/CXCL13 concentrations and renal expression of CXCL13/CXCR5 in patients with systemic lupus erythematosus and lupus nephritis", J. Rheum. 37(1):45-52, 2010.

Schiffer et al., "Short Term Administration of Costimulatory Blockade and Cyclophosphamide Induces Remission of Systemic Lupus Erythematosus Nephritis in NZB/W F1 Mice by a Mechanism Downstream of Renal Immune Complex Deposition", J. Immun. 171:489-497, 2003.

Sansonno et al., "Increased serum levels of the chemokine CXCL13 and up-regulation of its gene expression are distinctive features of HCV-related cryoglobulinemia and correlate with active cutaneous vasculitis", Blood, vol. 112(5):1620-1627, 2008.

De Padilla et al., "Extranodal Lymphoid Microstructures in Inflamed Muscle and Disease Severity of New-Onset Juvenile Dermatomyositis", Arthritis & Rheumatism 60(4):1160-1172, 2009.

Matsumoto et al., "CDR3 Spectratyping Analysis of the TCR Repertoire in Myasthenia Gravis", J. Immuno. 176:5100-5107, 2006.

Meraouna et al., "The chemokine CXCL13 is a key molecule in autoimmune myasthenia gravis", Blood, vol. 108(2):432-440, 2006.

Saito et al., "Altered expression of chemokine receptor CXCR5 on T cells of Myasthenia Gravis patients", Journal of Neuroimmunology, vol. 170:172-178, 2005. Abstract.

Forster et al."Expression of the G-protein-coupled receptor BLR1 defines mature, recirculating B cells and a subset of T-helper memory cells", Blood, vol. 84:830-840, 1994.

Forster et al., "A Putative Chemokine Receptor, BLR1, Directs B Cell Migration to Defined Lymphoid Organs and Specific Anatomic Compartments of the Spleen", Cell, vol. 87:1037-1047, 1996.

Zaldumbide et al., "A potentially immunologically inert derivative of the reverse tetracycline-controlled transactivator", Biotechnology Letters, vol. 32, 749-754, 2010.

Büttner et al., "Inflammaging impairs peripheral nerve maintenance and regeneration" Aging Cell—vol. 17, Issue 6, 15 pages.

Kizil et al., "Adult neurogenesis and brain regeneration in zebrafish" vol. 72, Issue3—Special Issue: Zebrafish Neurobiology: From Development to Circuit Function and Behaviour—Mar. 2012—pp. 429-461.

Chen, M., Yang, Y., Zhang, W. et al. Long Noncoding RNA SNHG5 Knockdown Alleviates Neuropathic Pain by Targeting the miR-154-5p/CXCL13 Axis. Neurochem Res 45, 1566-1575 (2020). https://doi.org/10.1007/s11064-020-03021-2.

Verdú et al., "Influence of aging on peripheral nerve function and regeneration" vol. 5, Issue4—Dec. 2000 pp. 191-208.

International Search Report and Written Opinion for the International Patent Application No. PCT/US2021/036298, dated Oct. 14, 2021, 17 pages.

Bauder et al., "Reproducible Mouse Sciatic Nerve Crush and Subsequent Assessment of Regeneration by Whole Mount Muscle Analysis", J Vis Exp (60), e3606 10.3791/3606, DOI : 10.3791/3606 (2012).

Keren et al., "B-cell depletion reactivates B lymphopoiesis in the BM and rejuvenates the B lineage in aging", Blood. 117(11):3104-3112 (2011) DOI 10.1182/blood-2010-09-307983.

Szklarczyk et al., "STRING v11: protein-protein association networks with increased coverage, supporting functional discovery in genome-wide experimental datasets", Nucl Acids Res 49:D607-D613 (2019) doi: 10.1093/nar/gky1131.

\* cited by examiner

Figure 4
FIG. 4A
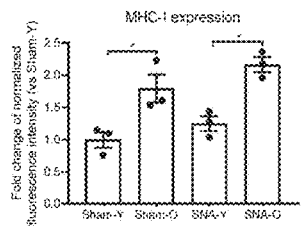
FIG. 4B
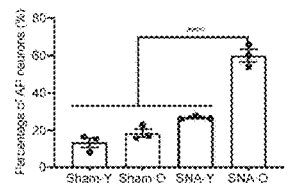
FIG. 4C Immune-evasive dox-inducible system
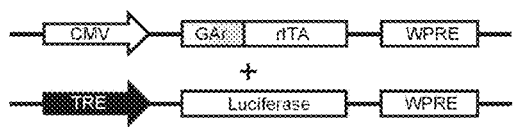
FIG. 4D
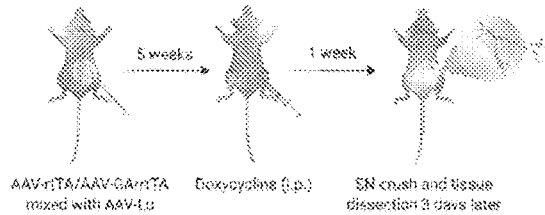
FIG. 4E
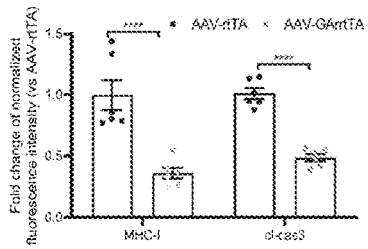
FIG. 4F
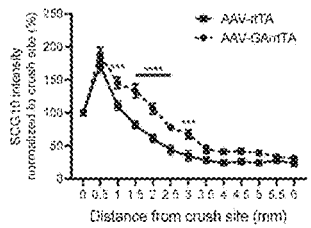
FIG. 4G
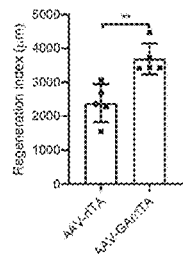

SEQUENCE LISTING

<160> NUMBER OF SEQ ID NOS: 34

<210> SEQ ID NO 1
<211> LENGTH: 109
<212> TYPE: PRT
<213> ORGANISM: Homo sapiens

<400> SEQUENCE: 1

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
            20                  25                  30

Cys Arg Cys Val Gln Glu Ser Ser Val Phe Ile Pro Arg Arg Phe Ile
        35                  40                  45

Asp Arg Ile Gln Ile Leu Pro Arg Gly Asn Gly Cys Pro Arg Lys Glu
    50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105

<210> SEQ ID NO 2
<211> LENGTH: 1219
<212> TYPE: DNA
<213> ORGANISM: Homo sapiens

<400> SEQUENCE: 2
gagaagatgt ttgaaaaaac tgactctgct aatgagcctg gactcagagc tcaagtctga      60
actctacctc cagacagaat gaagttcatc tcgacatctc tgcttctcat gctgctggtc     120
agcagcctct ctccagtcca aggtgttctg gaggtctatt acacaagctt gaggtgtaga     180
tgtgtccaag agagctcagt ctttatccct agacgcttca ttgatcgaat tcaaatcttg     240
ccccgtggga atggttgtcc aagaaaagaa atcatagtct ggaagaagaa caagtcaatt     300
gtgtgtgtgg accctcaagc tgaatggata caaagaatga tggaagtatt gagaaaaaga     360
agttcttcaa ctctaccagt tccagtgttt aagagaaaga ttccctgatg ctgatatttc     420
cactaagaac acctgcattc ttcccttatc cctgctctgg attttagttt tgtgcttagt     480
taaatctttt ccaggaaaaa gaacttcccc atacaaataa gcatgagact atgtaaaaat     540
aaccttgcag aagctgatgg ggcaaactca agcttcttca ctcacagcac cctatataca     600
cttggagttt gcattcttat tcatcaggga ggaaagtttc tttgaaaata gttattcagt     660
tataagtaat acaggattat tttgattata tacttgttgt ttaatgttta aaatttctta     720
gaaaacaatg gaatgagaat ttaagcctca aatttgaaca tgtggcttga attaagaaga     780
aaattatggc atatattaaa agcaggcttc tatgaaagac tcaaaaagct gcctgggagg     840
cagatggaac ttgagcctgt caagaggcaa aggaatccat gtagtagata tcctctgctt     900
aaaaactcac tacggaggag aattaagtcc tacttttaaa gaatttcttt ataaaattta     960
ctgtctaaga ttaatagcat tcgaagatcc ccagacttca tagaatactc agggaaagca    1020 tttaagggt gatgtacaca tgtatccttt cacacatttg ccttgacaaa cttctttcac    1080
tcacatcttt ttcactgact tttttgtgg ggggcgggc cgggggact ctggtatcta    1140 attctttaat gattcctata aatctaatga cattcaataa agttgagcaa acattttact    1200

```
taaaaaaaaa aaaaaaaaa                                                 1219
```

<210> SEQ ID NO 3
<211> LENGTH: 109
<212> TYPE: PRT
<213> ORGANISM: Mus musculus

<400> SEQUENCE: 3

```
Met Arg Leu Ser Thr Ala Thr Leu Leu Leu Leu Ala Ser Cys Leu
1               5                   10                  15

Ser Pro Gly His Gly Ile Leu Glu Ala His Tyr Thr Asn Leu Lys Cys
            20                  25                  30

Arg Cys Ser Gly Val Ile Ser Thr Val Val Gly Leu Asn Ile Ile Asp
        35                  40                  45

Arg Ile Gln Val Thr Pro Pro Gly Asn Gly Cys Pro Lys Thr Glu Val
    50                  55                  60

Val Ile Trp Thr Lys Met Lys Lys Val Ile Cys Val Asn Pro Arg Ala
65                  70                  75                  80

Lys Trp Leu Gln Arg Leu Leu Arg His Val Gln Ser Lys Ser Leu Ser
                85                  90                  95

Ser Thr Pro Gln Ala Pro Val Ser Lys Arg Arg Ala Ala
            100                 105
```

<210> SEQ ID NO 4
<211> LENGTH: 1162
<212> TYPE: DNA
<213> ORGANISM: Mus musculus

<400> SEQUENCE: 4

```
gagctaaagg ttgaactcca cctccaggca gaatgaggct cagcacagca acgctgcttc    60
tcctcctggc cagctgcctc tctccaggcc acggtattct ggaagcccat tacacaaact   120
taaaatgtag gtgttctgga gtgatttcaa ctgttgtcgg tctaaacatc atagatcgga   180
ttcaagttac gcccctggg aatggctgcc ccaaaactga agttgtgatc tggaccaaga   240
tgaagaaagt tatatgtgtg aatcctcgtg ccaaatggtt acaagagatta ttaagacatg   300 tccaaagcaa aagtctgtct tcaactcccc aagctccagt gagtaagaga agagctgcct   360
gaagccacta tcatctcaaa agacacacct gcacctttt ttttatccct gctctgaatt    420
ttagatatgt tcttagttaa agaatttcca agaaaataac tcccctctac aaacaaacat    480
gactgtaggt aaaacaaagc aaaaacaaac aagcaaacaa acaaactaaa aaaaacccaa    540
tcctgcagga gctgagaggg aatgctcaag ctccgttgca tacccaaccc acatccttgt    600
tccttaagaa aggctatttg agaacaggca tttagtgaca acccacttca gatgcatgtg    660
gtaatagatc tgttgtttaa tgttaaacta tcctagattg tcgaggaatg aaaaacctac    720
atgtcaaatg tgaacttgta gctcgtacta acaagaggtt tgcgagatgg acttcagtta    780
ttttgcaccc ttgtaaaacg caggcttcca aaatagtctc cagaaggttc ctgggaagct    840
ggtgcaatgc catcatgagg tggtgcaaag caggtctcct ttagagaaaa gcttcctggg    900
ggaaacagtc ctactttgaa aggttgcttg tataagattt attgtcttgc attaaaacca    960
gtaacaattg aaagatcctc agcttaaagg tccaggctct tcagcagtat acaaatatat   1020
tcctttgcac tgtgacccctg atgatctatt tttattattc atatctttca cacagacaaa   1080
ataccagcct cttgtatcag attctttaat gtttcctatt catctggtgt cattcaataa   1140
atgtaatcaa atgtttttgct ta                                            1162
```

```
<210> SEQ ID NO 5
<211> LENGTH: 82
<212> TYPE: PRT
<213> ORGANISM: Macaca fascicularis

<400> SEQUENCE: 5

Val Leu Glu Val Tyr Tyr Thr His Leu Arg Cys Arg Cys Val Gln Glu
1               5                   10                  15

Ser Ser Val Phe Ile Pro Arg Arg Phe Ile Asp Arg Ile Gln Ile Ser
            20                  25                  30

Pro Arg Gly Asn Gly Cys Pro Arg Lys Glu Ile Ile Val Trp Lys Lys
        35                  40                  45

Asn Lys Ser Val Val Cys Val Asp Pro Gln Ala Glu Trp Ile Gln Arg
    50                  55                  60

Ile Met Glu Met Leu Arg Lys Lys Ser Ser Thr Pro Pro Val Pro
65                  70                  75                  80

Val Phe

<210> SEQ ID NO 6
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Gln Glu Ser Gly Pro Gly Ile Leu Gln Pro Ser Gln
1               5                   10                  15

Thr Leu Asn Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Arg Tyr Asn Pro Ala
    50                  55                  60

Leu Lys Ser Arg Leu Thr Ile Ser Lys Glu Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Thr Arg Ile Ala Gly Tyr Tyr Gly Ser Arg Asp Trp Phe Ala Tyr
            100                 105                 110

Trp Gly Gln Gly Thr Thr Val Thr Val Ser Ser
        115                 120

<210> SEQ ID NO 7
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Ser
            20                  25                  30

Gly Ile Ser Phe Met His Trp Tyr Gln Gln Lys Pro Gly Gln Pro Pro
        35                  40                  45
```

```
Lys Leu Leu Ile Phe Arg Ala Ser Asp Leu Glu Ser Gly Ile Pro Ala
 50                  55                  60

Arg Phe Ser Gly Ser Gly Ser Arg Thr Asp Phe Thr Leu Thr Val Asn
 65                  70                  75                  80

Pro Val Glu Thr Asp Asp Val Ala Thr Tyr Phe Cys Gln Gln Ser Asn
                 85                  90                  95

Lys Asp Pro Trp Thr Phe Gly Gly Gly Thr Lys Leu Glu Ile Lys
                100                 105                 110

<210> SEQ ID NO 8
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Pro Gly Leu Val Lys Pro Ser Glu
1                5                  10                  15

Thr Leu Ser Leu Thr Cys Thr Val Ser Gly Phe Ser Leu Ser Thr Phe
                 20                  25                  30

Gly Met Gly Val Gly Trp Ile Arg Gln Pro Pro Gly Lys Gly Leu Glu
         35                  40                  45

Trp Ile Ala His Ile Trp Trp Asp Asp Arg Arg Tyr Asn Pro Ala
 50                  55                  60

Leu Lys Ser Arg Val Thr Ile Ser Lys Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ile Ala Gly Tyr Tyr Gly Ser Arg Asp Trp Phe Ala Tyr
                100                 105                 110

Trp Gly Gln Gly Thr Thr Val Thr Val Ser Ser
        115                 120

<210> SEQ ID NO 9
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1                5                  10                  15

Asp Arg Val Thr Ile Thr Cys Arg Ala Ser Glu Ser Val Asp Asn Ser
                 20                  25                  30

Gly Ile Ser Phe Met His Trp Tyr Gln Gln Lys Pro Gly Lys Ala Pro
         35                  40                  45

Lys Leu Leu Ile Phe Arg Ala Ser Asp Leu Glu Ser Gly Val Pro Ser
 50                  55                  60

Gly Phe Ser Gly Ser Gly Ser Arg Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Lys Asp Pro Trp Thr Phe Gly Gln Gly Thr Lys Leu Glu Ile Lys
                100                 105                 110
```

```
<210> SEQ ID NO 10
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Thr Phe
            20                  25                  30

Gly Met Gly Val Gly Trp Ile Arg Gln Pro Pro Gly Lys Gly Leu Glu
        35                  40                  45

Trp Ile Ala His Ile Trp Trp Asp Asp Arg Arg Tyr Asn Pro Ala
    50                  55                  60

Leu Lys Ser Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ile Ala Gly Tyr Tyr Gly Ser Arg Asp Trp Phe Ala Tyr
            100                 105                 110

Trp Gly Gln Gly Thr Thr Val Thr Val Ser Ser
        115                 120

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Met
            20                  25                  30

Gly Ile Ser Phe Met His Trp Tyr Gln Gln Lys Pro Gly Lys Ala Pro
        35                  40                  45

Lys Leu Leu Ile Phe Arg Ala Ser Asp Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Lys Asp Pro Trp Thr Phe Gly Gln Gly Thr Lys Leu Glu Ile Lys
            100                 105                 110

<210> SEQ ID NO 12
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

```
Gln Val Gln Leu Lys Glu Ser Gly Pro Gly Ile Leu Pro Ser Gln
1               5                   10                  15

Thr Leu Ser Leu Thr Cys Ser Phe Ser Gly Phe Ser Leu Ser Thr Phe
            20                  25                  30

Asn Met Gly Val Gly Trp Ile Arg Arg Pro Ser Gly Lys Gly Leu Glu
            35                  40                  45

Trp Leu Thr His Ile Trp Trp Asp Asp Lys Tyr Tyr Asn Pro Ala
50                  55                  60

Leu Arg Asn Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Arg Leu Gly Gln Tyr Asp Tyr Asp Glu Gly Phe Asp Tyr
                100                 105                 110

Trp Gly Gln Gly Thr Thr Val Thr Val Ser Ser
            115                 120
```

```
<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Leu Leu Ile Phe Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
                100                 105                 110
```

```
<210> SEQ ID NO 14
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Ala Thr Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Asn Pro Ser
50                  55                  60
```

```
Leu Arg Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Leu Gly Gln Tyr Asp Tyr Asp Glu Gly Phe Asp Tyr
            100                 105                 110

Trp Gly Gln Gly Thr Thr Val Thr Val Ser Ser
        115                 120
```

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Val Val Met Thr Gln Thr Pro Leu Ser Leu Pro Val Thr Pro Gly
 1                   5                  10                  15

Glu Pro Ala Ser Ile Ser Cys Arg Ser Ser Gln Ser Leu Leu Asp Ser
                 20                  25                  30

Tyr Asn Gly Asn Thr Tyr Leu Ala Trp Tyr Leu Arg Lys Pro Gly Gln
             35                  40                  45

Ser Pro Gln Leu Leu Ile Tyr Arg Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Ser Gln
                 85                  90                  95

Ser Thr His Val Pro Tyr Thr Phe Gly Gln Gly Thr Lys Leu Glu Ile
            100                 105                 110

Lys
```

<210> SEQ ID NO 16
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Val Thr Leu Lys Glu Ser Gly Pro Ala Leu Val Lys Pro Thr Gln
 1                   5                  10                  15

Thr Leu Thr Leu Thr Cys Thr Phe Ser Gly Phe Ser Leu Ser Thr Phe
                 20                  25                  30

Asn Met Gly Val Gly Trp Ile Arg Gln Pro Pro Gly Lys Ala Leu Glu
             35                  40                  45

Trp Leu Thr His Ile Trp Trp Asp Asp Lys Tyr Tyr Asn Pro Ala
 50                  55                  60

Leu Arg Asn Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Leu Gly Gln Tyr Asp Tyr Asp Glu Gly Phe Asp Tyr
            100                 105                 110

Trp Gly Gln Gly Thr Leu Val Thr Val Ser Ser
```

-continued

```
                115                 120

<210> SEQ ID NO 17
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                  10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Phe Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Phe Gly Met Gly Val Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Thr Phe Asn Met Gly Val Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Thr Phe Gly Ala Thr Val Gly
1               5

<210> SEQ ID NO 21
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Ile Trp Trp Asp Asp Asp Arg Arg Tyr Asn Pro Ala Leu Lys Ser
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Leu Thr His Ile Trp Trp Asp Asp Asp Lys Tyr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Leu Ala Leu Ile Tyr Trp Asp Asp Asp Lys Arg
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Ala Gly Tyr Tyr Gly Ser Arg Asp Trp Phe Ala Tyr
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Arg Arg Leu Gly Gln Tyr Asp Tyr Asp Glu Gly Phe Asp
1               5                   10

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Ser Glu Ser Val Asp Asn Ser Gly Ile Ser Phe Met His
```

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ala Ser Glu Ser Val Asp Asn Met Gly Ile Ser Phe Met His
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Ser Asn Gly Asn Thr Tyr Leu His Trp Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Ser Tyr Asn Gly Asn Thr Tyr Leu Ala Trp Tyr
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Asp Leu Glu Ser
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Leu Ile Phe Lys Val Ser Asn Arg Phe
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic

```
              peptide

<400> SEQUENCE: 32

Leu Leu Ile Tyr Arg Leu Ser Tyr Arg Ala
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Ser Asn Lys Asp Pro Trp Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Gln Ser Thr His Val Pro Tyr
1               5
```

USE OF CXCL13 BINDING MOLECULES TO PROMOTE PERIPHERAL NERVE REGENERATION

CROSS REFERENCE TO RELATED APPLICATIONS

This is a non-provisional of U.S. provisional application Ser. No. 63/037,755, filed Jun. 11, 2020, the entirety of which application is incorporated by reference herein.

BACKGROUND

Axonal injuries to the nervous system increasingly occur in an expanding aging population (DeVivo, M. J., and Chen, Y. (2011). Archives of Physical Medicine and Rehabilitation 92, 332-338; Singh et al., (2014). Clinical Epidemiology 6, 309). Unfortunately, the axonal regenerative ability and repair processes decline with aging, undermining functional recovery and increasing long-term disability (Nagano, A. (1998). Journal of Orthopaedic Science 3, 71-80; Pestronk et al., (1980). Experimental Neurology 70, 65-82; Tanaka and deF. Webster, (1991). Journal of Comparative Neurology 308, 180-187; Vaughan, 1992. Journal of Comparative Neurology, 323, 219-237; Verdú et al., (2000). Journal of the Peripheral Nervous System 5, 191-208.

Our understanding of the cellular and molecular mechanisms of this aging-dependent regenerative decline is very sparse. Studies have shown that an age-related impairment in de-differentiation and activation of Schwann cells (SCs) limits axonal regrowth in the injured peripheral nervous system (PNS), impairing sensory and motor recovery (Kang and Lichtman, (2013). Journal of Neuroscience 33, 19480-19491; Painter et al., (2014). Neuron 83, 331-343). In the central nervous system, following spinal cord injury, deletion of phosphatase and tensin homolog (PTEN) with a concomitant increase in mTOR signaling only partially limits the aging-dependent axonal regenerative decay of corticospinal tracts (Geoffroy et al., (2016). Cell Reports 15, 238-246). These studies addressed some of the molecular mechanisms underpinning the aging-dependent molecular changes following an injury, however, aging in itself leads to profound modifications in cell signaling, metabolism, immunity, gene regulation and protein translation in every tissue affecting homeostasis and predisposing to disease (Barzilai et al., (2012). Diabetes 61, 1315-1322; Lardenoije et al., (2015). Progress in Neurobiology 131, 21-64; Pomatto and Davies, (2017). The Journal of Physiology 595, 7275-7309; Taylor and Dillin, (2011). Cold Spring Harbor Perspectives in Biology 3, a004440; Weiskopf et al., (2009). Transplant International 22, 1041-1050).

Thus, there is a need to determine the factors driving aging-dependent regulation in neurons and the role of those factors in the control of axonal regeneration so that therapies that target such factors can be developed for the treatment of peripheral nervous system injuries.

FIELD

The invention relates to the use of CXCL13 neutralizing binding molecules, e.g., antibodies and antigen binding fragments thereof for the promotion of peripheral nerve regeneration in subjects with aging-dependent regeneration decline.

BRIEF SUMMARY OF THE DISCLOSURE

Methods for using CXCL13 binding molecules to promote peripheral nerve regeneration in a subject having aging-dependent regeneration decline are disclosed herein. According to aspects of the disclosure illustrated herein, there is provided a method for improving peripheral nerve regeneration in a subject with a peripheral nerve injury and aging-dependent regenerative decline including administering to the subject an effective amount of an isolated binding molecule which specifically binds to CXCL13 and inhibits, suppresses, prevents, reverses or slows the effect of CXCL13.

Methods for promoting nerve regeneration of an injured peripheral nerve in a subject with aging-dependent regenerative decline are provided, comprising administering to the subject an effective amount of an antibody or antigen-binding fragment thereof which specifically binds CXCL13. In certain embodiments of the methods, the antibody or antigen-binding fragment thereof inhibits CXCL13 activity. In certain embodiments of the methods, the inhibited CXCL13 activity is recruitment of CXCR5+CD8+ T cells to the dorsal root ganglion (DRG) of the injured peripheral nerve. In certain embodiments of the methods, the isolated antibody or antigen-binding fragment thereof inhibits CXCL13 interaction with its receptor. In certain embodiments of the methods, the CXCL13 receptor is CXCR5. In certain embodiments of the methods, the isolated antibody or antigen-binding fragment thereof competitively inhibits a reference monoclonal antibody selected from the group consisting of Mab 5378, MAb 5261, MAb5080, MAb 1476, 3D2, 3C9, MAb 5091, MAb 1758, or MAb 0745 from specifically binding to CXCL13. In certain embodiments of any one of the aforementioned methods, the isolated antibody or antigen-binding fragment thereof specifically binds to the same CXCL13 epitope as a reference monoclonal antibody selected from the group consisting of Mab 5378, MAb 5261, MAb 5080, MAb 1476, 3D2, 3C9, MAb 5091, MAb 1758, or MAb 0745. In certain embodiments of the methods, the antibody or antigen-binding fragment thereof comprises (A) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs: 26, 30, and 33, respectively; (B) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs:27, 30, and 33, respectively; (C) a VH comprising heavy chain complementarity determining region 1 (VH-CDR1), VH-CDR2, and VH-CDR3 amino acid sequences set forth as SEQ ID NOs:19, 22, and 25, respectively; and a VL comprising light chain complementarity determining region 1 (VL-CDR1), VL-CDR2, and VL-CDR3 amino acid sequences set forth as SEQ ID NOs:28, 31, and 34, respectively; or (D) a VH comprising heavy chain complementarity determining region 1 (VH-CDR1), VH-CDR2, and VH-CDR3 amino acid sequences set forth as SEQ ID NOs:20, 23, and 25, respectively; and a VL comprising light chain complementarity determining region 1 (VL-CDR1), VL-CDR2, and VL-CDR3 amino acid sequences set forth as SEQ ID NOs:29, 31, and 34, respectively. In certain embodiments, the VH and VL of the antibody or antigen-binding fragment thereof comprise amino acid sequences identical to VH and VL sequences selected from the group consisting of: (i) SEQ ID NO: 6 and SEQ ID NO:7, respectively; (ii) SEQ ID NO: 8 and SEQ ID NO: 9, respectively; (iii) SEQ ID NO: 10 and SEQ ID NO:11, respectively; (iv) SEQ ID NO:12 and SEQ ID NO:13, respectively; (v) SEQ ID NO:14 and SEQ ID NO:15, respectively; and (vi) SEQ ID NO:16 and SEQ ID NO:17, respectively. In certain embodiments, the isolated binding molecule is MAb 5261, MAb 5091, or MAb 1476, MAb 1758. In certain embodiments of any one of the aforementioned methods, the injured peripheral nerve is selected from the group consisting of sciatic nerve, peroneal nerve, spinal accessory nerve, and brachial plexus. In certain embodiments of any of the aforementioned methods, the method regenerates the injured nerve totally or partially, reinnervates epidermal tissue, or results in complete or partial recovery of neurological function of the injured nerve, or a combination thereof.

Methods for treatment of peripheral nerve injury in a subject with aging-dependent regenerative decline and a peripheral nerve injury are provided, comprising administering to the subject an effective amount of an isolated antibody or antigen-binding fragment thereof which specifically binds CXCL13. In certain embodiments of the methods, the peripheral nerve injury is the result of pressure, stretching or cutting of the peripheral nerve. In certain embodiments of the methods, the peripheral nerve injury is an injury of the sciatic nerve, brachial plexus, peroneal nerve, or spinal accessory nerve. In certain embodiments of the methods, the peripheral nerve injury is a sciatic nerve injury. In certain embodiments of any of the aforementioned methods, the antibody or antigen-binding fragment thereof inhibits CXCL13 interaction with its receptor. In certain embodiments of any of the aforementioned methods, the receptor is CXCR5. In certain embodiments of any of the aforementioned methods, the antibody or antigen-binding fragment thereof comprises: (A) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs: 26, 30, and 33, respectively; (B) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs:27, 30, and 33, respectively; (C) a VH comprising heavy chain complementarity determining region 1 (VH-CDR1), VH-CDR2, and VH-CDR3 amino acid sequences set forth as SEQ ID NOs:19, 22, and 25, respectively; and a VL comprising light chain complementarity determining region 1 (VL-CDR1), VL-CDR2, and VL-CDR3 amino acid sequences set forth as SEQ ID NOs:28, 31, and 34, respectively; or (D) a VH comprising heavy chain complementarity determining region 1 (VH-CDR1), VH-CDR2, and VH-CDR3 amino acid sequences set forth as SEQ ID NOs:20, 23, and 25, respectively; and a VL comprising light chain complementarity determining region 1 (VL-CDR1), VL-CDR2, and VL-CDR3 amino acid sequences set forth as SEQ ID NOs:29, 31, and 34, respectively. In certain embodiments of any of the aforementioned methods, the VH and VL of said antibody or antigen-binding fragment thereof comprise amino acid sequences identical to VH and VL sequences selected from the group consisting of: (i). SEQ ID NO: 6 and SEQ ID NO:7, respectively; (ii) SEQ ID NO: 8 and SEQ ID NO: 9, respectively; (iii) SEQ ID NO: 10 and SEQ ID NO:11, respectively; (iv) SEQ ID NO:12 and SEQ ID NO:13, respectively; (v) SEQ ID NO:14 and SEQ ID NO:15, respectively; and (vi) SEQ ID NO:16 and SEQ ID NO:17, respectively. In certain embodiments of any of the aforementioned methods, the isolated binding molecule is a human or humanized antibody that competitively inhibits a reference monoclonal antibody selected from the group consisting of Mab 5378, MAb 5261, MAb5080, MAb1476, MAb 5091, MAb 1758, 3D2 and 3C9 from specifically binding to CXCL13. In certain embodiments of any of the aforementioned methods, the isolated binding molecule is MAb 5261, MAb 5091, MAb 1476, or MAb 1758.

Methods for reversing aging-dependent regenerative decline in a subject in need thereof are provided, comprising administering to the subject an effective amount of an isolated antibody or antigen-binding fragment thereof which specifically binds CXCL13. In certain embodiments of the methods, the antibody or antigen-binding fragment thereof inhibits CXCL13 interaction with its receptor. In certain embodiments of the methods, the receptor is CXR5. In certain embodiments of any of the aforementioned methods, the isolated antibody or antigen-binding fragment thereof competitively inhibits a reference monoclonal antibody selected from the group consisting of Mab 5378, MAb 5261, MAb5080, MAb1476, MAb 5091, MAb 1748, 3D2 and 3C9 from specifically binding to CXCL13. In certain embodiments of any of the aforementioned methods, the antibody or antigen-binding fragment thereof comprises: (A) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs: 26, 30, and 33, respectively; (B) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs:27, 30, and 33, respectively; (C) a VH comprising heavy chain complementarity determining region 1 (VH-CDR1), VH-CDR2, and VH-CDR3 amino acid sequences set forth as SEQ ID NOs:19, 22, and 25, respectively; and a VL comprising light chain complementarity determining region 1 (VL-CDR1), VL-CDR2, and VL-CDR3 amino acid sequences set forth as SEQ ID NOs:28, 31, and 34, respectively; or (D) a VH comprising heavy chain complementarity determining region 1 (VH-CDR1), VH-CDR2, and VH-CDR3 amino acid sequences set forth as SEQ ID NOs:20, 23, and 25, respectively; and a VL comprising light chain complementarity determining region 1 (VL-CDR1), VL-CDR2, and VL-CDR3 amino acid sequences set forth as SEQ ID NOs:29, 31, and 34, respectively. In certain embodiments of any of the aforementioned methods, the VH and VL of said antibody or antigen-binding fragment thereof comprise amino acid sequences identical to VH and VL sequences selected from the group consisting of: (i). SEQ ID NO: 6 and SEQ ID NO:7, respectively; (ii) SEQ ID NO: 8 and SEQ ID NO: 9, respectively; (iii) SEQ ID NO: 10 and SEQ ID NO:11, respectively; (iv) SEQ ID NO:12 and SEQ ID NO:13, respectively; (v) SEQ ID NO:14 and SEQ ID NO:15, respectively; and (vi) SEQ ID NO:16 and SEQ ID NO:17, respectively. In certain embodiments of any of the aforementioned methods, the isolated binding molecule is MAb 5261, MAb 5091, MAb 1476, or MAb 1758. In certain embodiments of any of the aforementioned methods, the subject has a peripheral nerve injury. In certain embodiments of any of the aforementioned methods, the peripheral injury is a sciatic nerve injury, brachial plexus injury, spinal accessory nerve injury, or peroneal nerve injury. In certain embodiments of any of the aforementioned methods, the peripheral nerve injury is a sciatic nerve injury.

BRIEF DESCRIPTION OF THE DRAWINGS/FIGURES

Figure 1B:
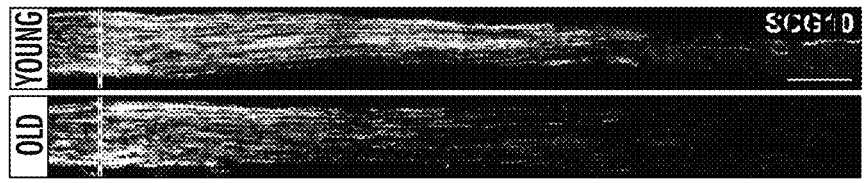
Figure 1C:
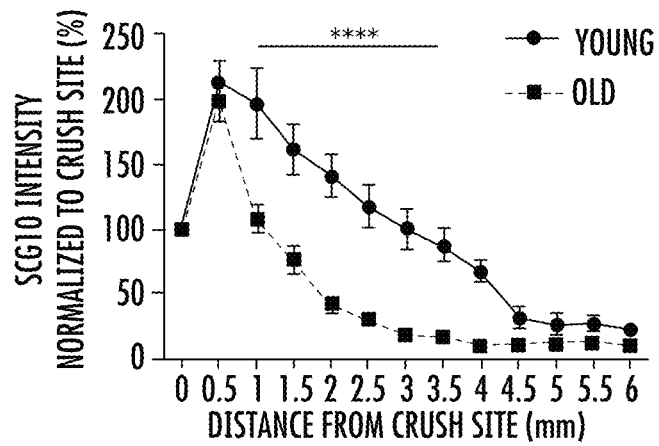
Figure 1D:
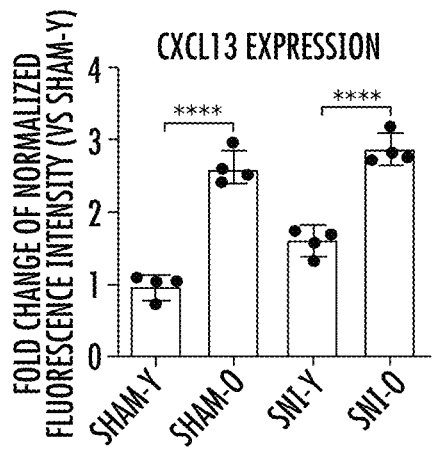
Figure 1E:
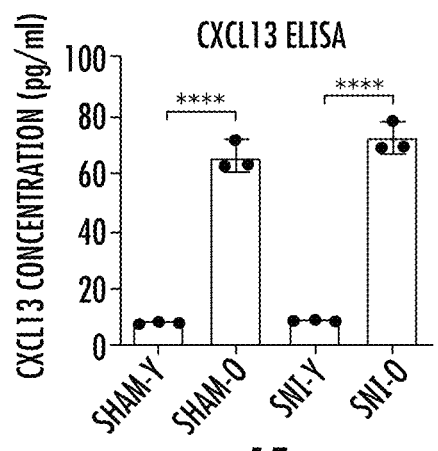

FIG. 1A-E shows that aging induces enrichment in chemokines/cytokines and adaptive immunity in dorsal root ganglia (DRG) preceding and following sciatic nerve injury. FIG. 1A is a heatmap showing the fold change of differentially expressed (DE) cytokines in the protein-protein network from sciatic nerve injury (SNI) young, SNI old versus sham young mice. FIG. 1B is SCG10 immunostaining of longitudinal sections of sciatic nerve of young and aged mice 3 days after sciatic crush injury. FIG. 1C shows normalized SCG10 intensity to the proximal crush site from young and aged mice (N=5, two-way ANOVA with post-hoc Sidak's test. P<0.01; P<0.0001). FIG. 1D Quantification of CXCL13 expression indicated by the fold change of normalized fluorescence intensity compared to the Sham Young (N=4, one-way ANOVA with post-hoc Tukey's test. P<0.0001). FIG. 1E CXCL13 ELISA from sciatic DRG (N=3, one-way ANOVA with post-hoc Tukey's test. **P<0.0001.

Figure 2A:
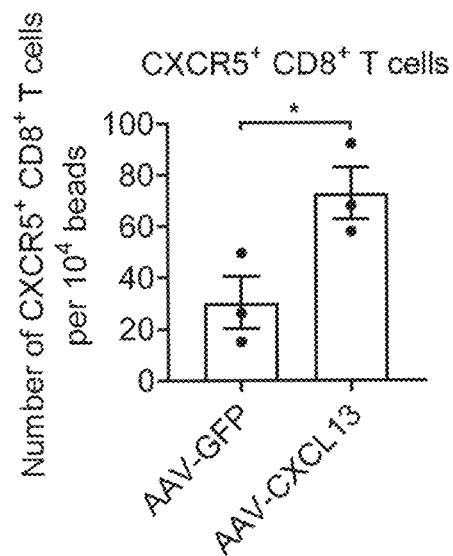
Figure 2B:
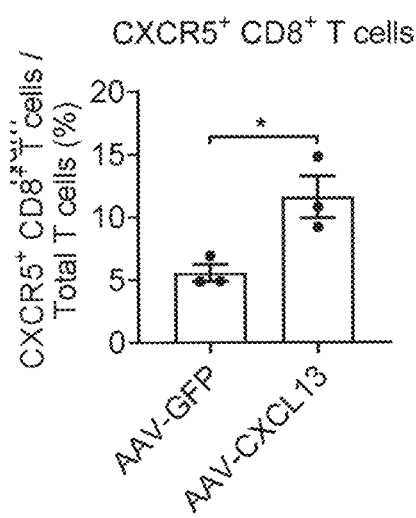
Figure 2C:
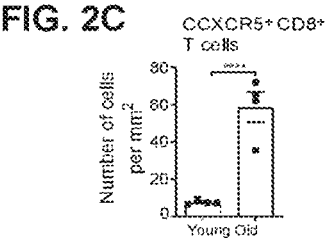
Figure 2D:
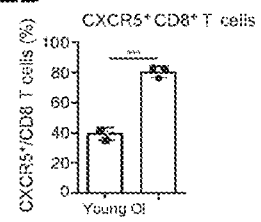

FIG. 2A-D show that CXCL13 is a chemoattractant for CXCR5+ and CD8 T cells which are enhanced in aged dorsal root ganglia (DRG). FIG. 2A: quantification of CXCR5+CD8+ T cell number normalized to the count beads in the sciatic DRG (N=3, Student's unpaired t-test. *P<0.05). FIG. 2B: percentage of CXCR5+CD8+T of total T cells in sciatic DRG (N=3, Student's unpaired t-test. *P<0.05). FIG. 2C: Quantification of CXCR5+CD8+ T cell number in the young and aged DRG 3 days after sciatic nerve injury (N=4, Student's unpaired t-test. **P<0.0001). FIG. 2D: Percentage of CXCR5+CD8+ T cells of total CD8 T cells from young and aged DRG sections immunostained for CXCR5 and CD8 3 days after nerve injury (N=3, Student's unpaired t-test. *P<0.001).

Figure 3:
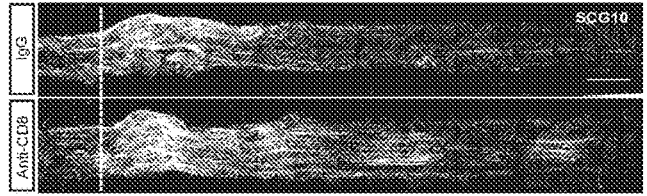
Figure 3:
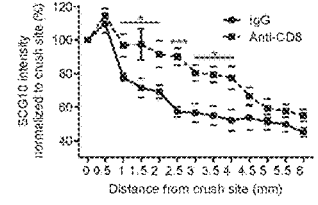
Figure 3:
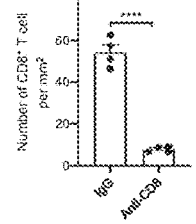

FIG. 3A-C demonstrates that CD8 T cells impede axonal regeneration of aged sciatic nerve. FIG. 3A: SCG10 immunostaining of longitudinal sections of sciatic nerve of aged mice 3 days after crush injury following control IgG or anti-CD8 monoclonal antibody. The dashed line indicates the proximal crush site. Scale bar: 500 m. FIG. 3B: Normalized SCG10 intensity to the proximal crush site in aged mice treated with control IgG (N=6) or anti-CD8 (N=6) monoclonal antibody (two-way ANOVA with post-hoc Sidak's test. *P<0.05, *P<0.001). FIG. 3C Quantification of the number of CD8 T cells in sciatic DRG sections 3 days after sciatic nerve injury following control IgG or anti-CD8 monoclonal antibody (N=3, Student's unpaired t-test was used. **P<0.0001).

FIG. 4A-G: demonstrates that MHC-1 expression is induced in aged DRG and is required for degenerative decline in mice following sciatic nerve injury. FIG. 4A: MHC-I and Tuj1 co-immunostaining and DAPI in sciatic DRG preceding or 3 days following sciatic nerve injury from young or aged mice. Fold change of MHC-I normalized fluorescence intensity (N=3, one-way ANOVA with post-hoc Tukey's test. *P<0.05). FIG. 4B: Percentage of antigen-presenting (AP) DRG neurons showing cell surface MHC-I expression in sciatic DRG from young or aged mice (N=3, one-way ANOVA with post-hoc Tukey's test. **P<0.0001). FIG. 4C: Linear diagram of dual vector doxycycline-inducible immune-evasive GAr system with luciferase reporter delivered by AAV viral particles. FIG. 4D: Experimental scheme. FIG. 4E: change of MHC-I and cleaved caspase3 normalized fluorescence intensity in DRG sections after AAV-rtTA or AAV-Gar-rtT infection and 3 days after sciatic nerve injury in aged mice (N=6, two-way ANOVA with post-hoc Sidak's test. P<0.0001). FIG. 4F: Normalized SCG10 intensity to the proximal crush site in aged mice infected with AAV-rtTA or AAV-GAr-rtTA (N=6, two-way ANOVA with post-hoc Sidak's test. *P<0.001, **P<0.0001). FIG. 4G: Regeneration index indicated by the distance from crush site when SCG10 intensity is reduced to 50% compared to the proximal injury site (N=5, Student's unpaired t-test was used. P<0.01).

Figure 5A:
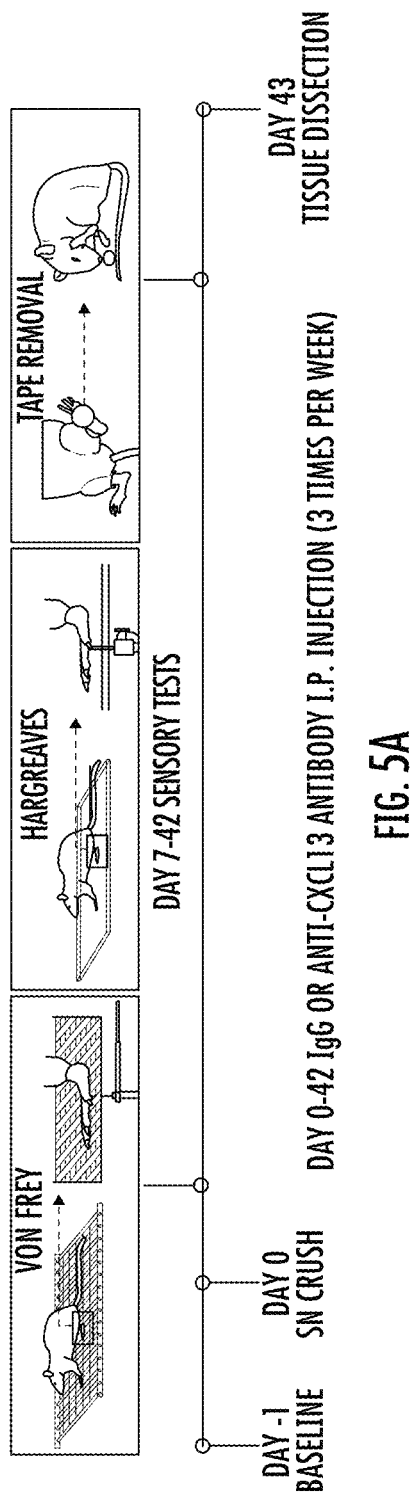
Figure 5B:
Figure 5C:
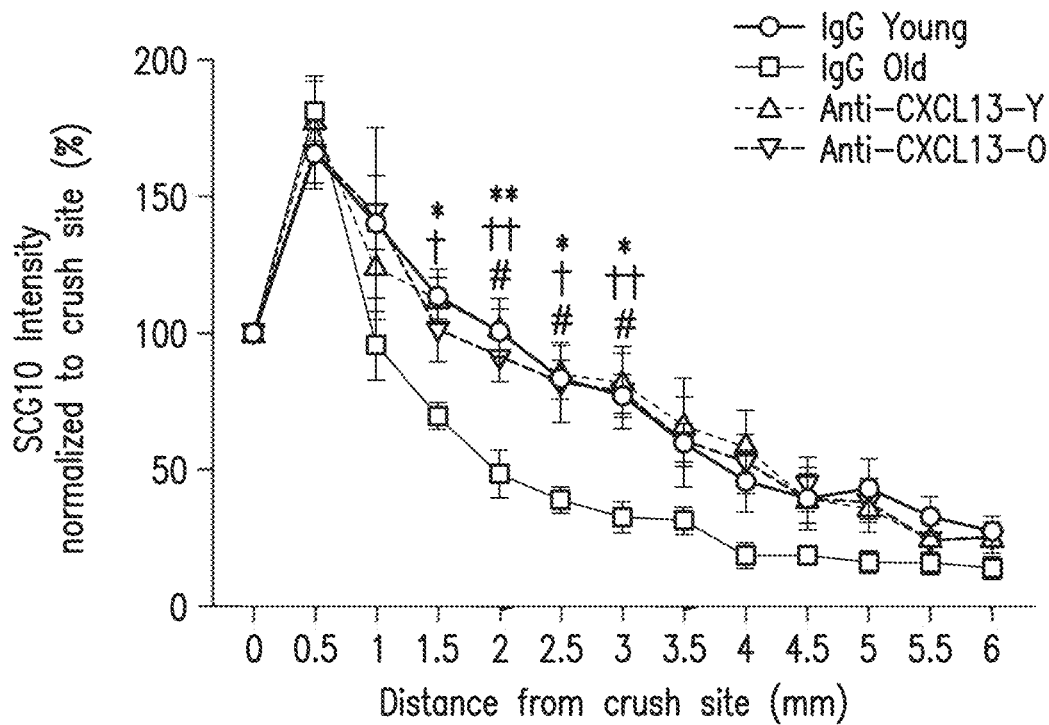
Figure 5D:
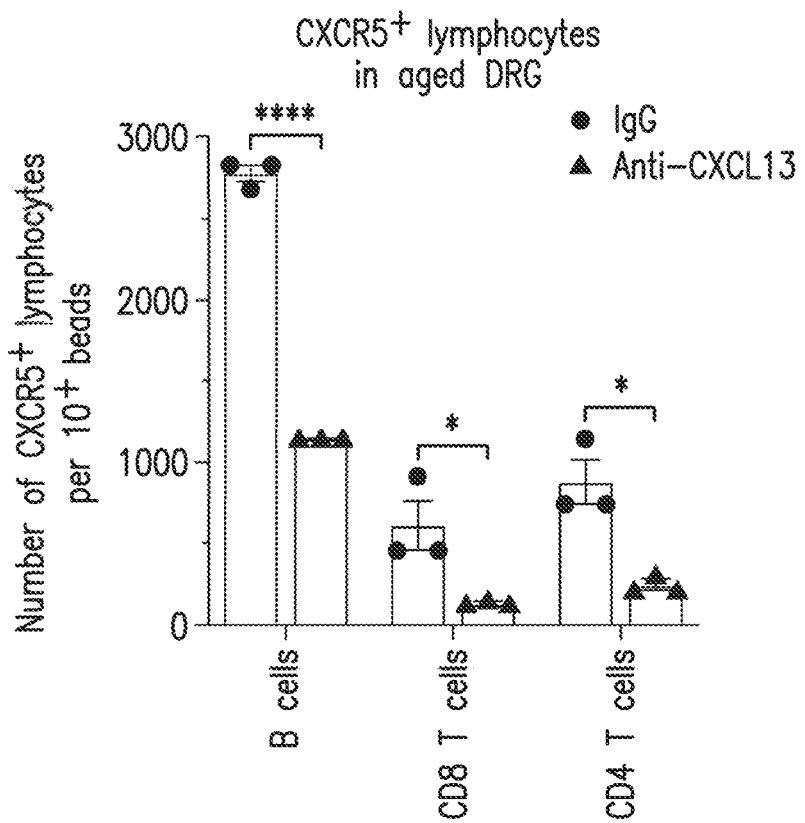
Figure 5E:
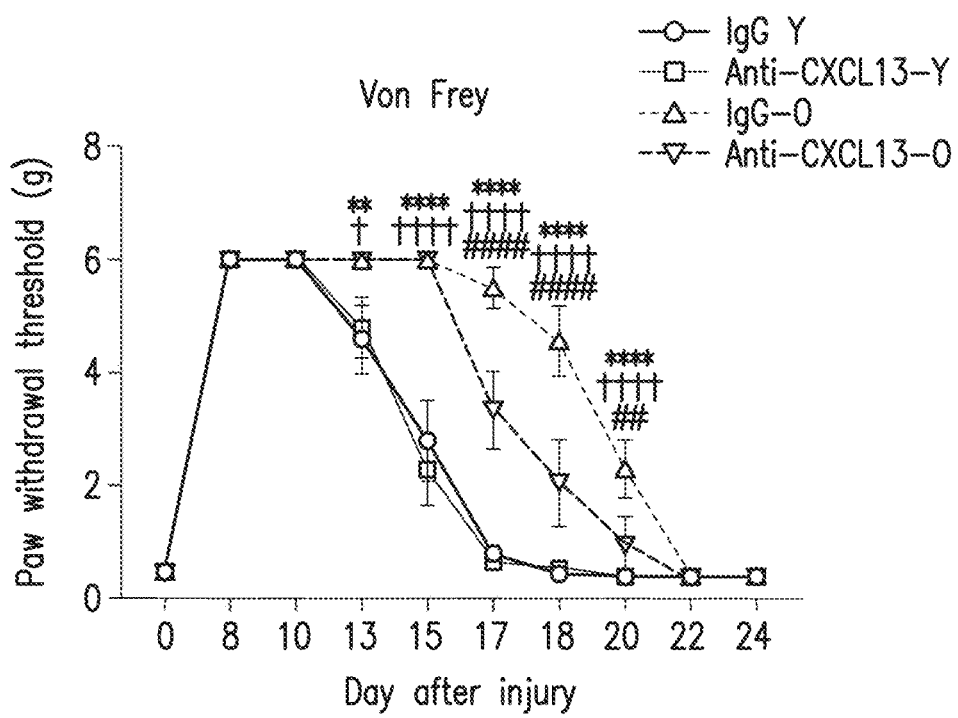
Figure 5F:
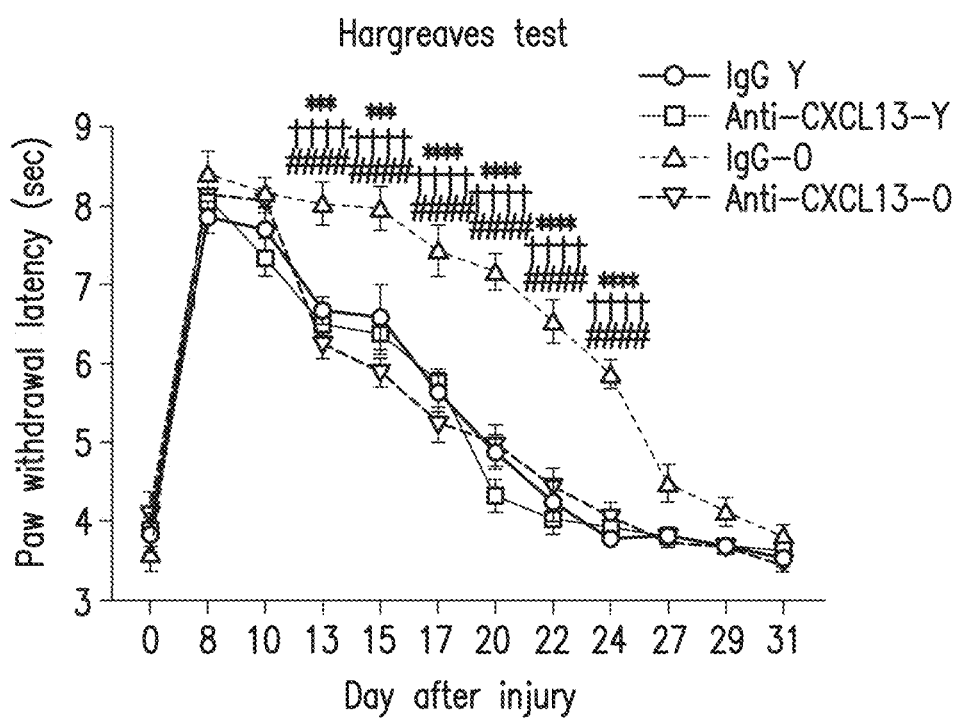
Figure 5G:
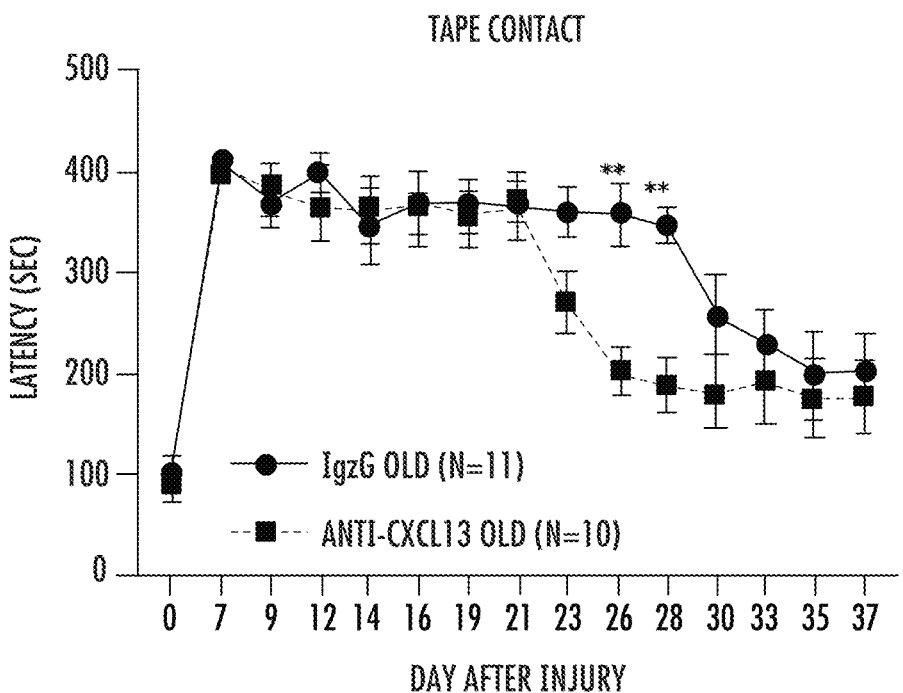
Figure 5H:
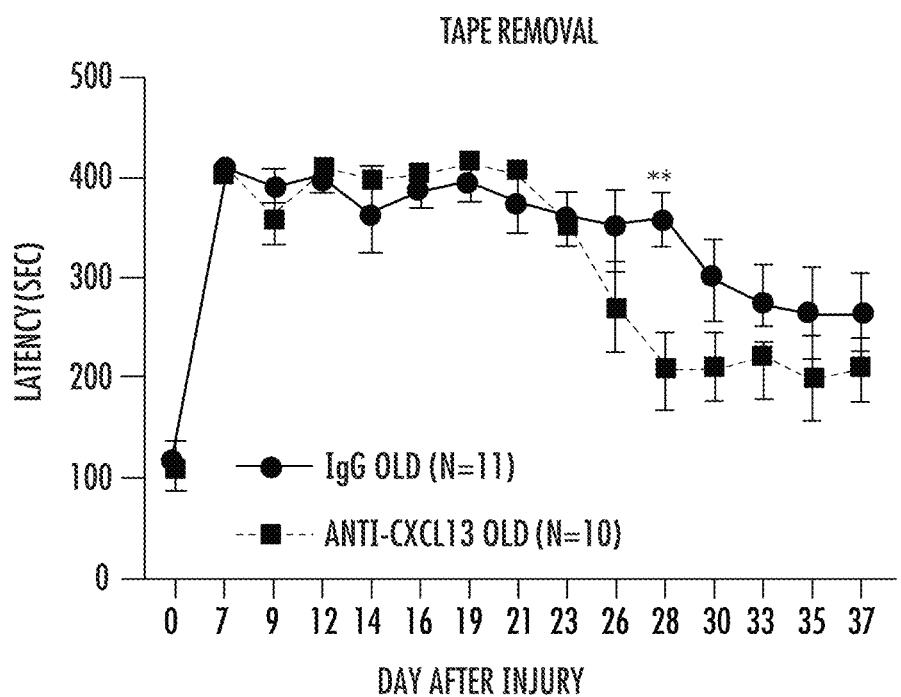

FIG. 5A-L: demonstrates the effects of neutralization of CXCL13. FIG. 5A: Schematic procedure of sensory functional assessment with chronic administration of anti-CXCL13 antibody after sciatic nerve crush. FIG. 5B: SCG10 immunostaining of longitudinal sciatic nerve sections from control IgG or anti-CXCL13 monoclonal antibody 3 days after sciatic nerve injury (SNI) in young and aged mice. The dashed line indicates the proximal injury site. Scale bar: 100 μm. FIG. 5C: Normalized SCG10 intensity to the proximal crush site from young or aged mice treated with IgG or anti-CXCL13 monoclonal antibody (N=6, two-way ANOVA with post-hoc Sidak's test. *P (BOLD)<0.05, **P (BOLDe)<0.01, IgG-Y vs IgG-O; *P (BLACK)<0.05, **P (BLACK)<0.01, anti-CXCL13-Y vs IgG-O; *P (GREY)<0.05, anti-CXCL13-O vs IgG-O). FIG. 5D: FACS quantification of CXCR5+B, CD8+ and CD4+ T cell number from DRG 3 days after sciatic nerve injury in aged mice. (N=3, two-way ANOVA with post-hoc Sidak's test. P<0.01, *P<0.001, **P<0.0001). FIG. 5E: Mechanical sensitivity by measuring the paw withdrawal threshold of the hind paw following stimulation with von Frey filaments after a unilateral sciatic nerve crush (N (IgG-Y)=10, N (anti-CXCL13-Y)=10, N (IgG-O)=11, N (anti-CXCL13-0)=10; two-way ANOVA with post-hoc Sidak's test. P<0.01, **P<0.0001, IgG-Y vs IgG-O; $P<0.05, $$$$$P<0.0001, anti-CXCL13-Y vs IgG-O; ##P<0.01, ####P<0.0001, anti-CXCL13-0 vs IgG-O). FIG. 5F: Thermo-sensitivity analysis by Hargreaves test measures the paw withdrawal latency of the hind paw after a unilateral sciatic nerve crush (N=10, two-way ANOVA with post-hoc Sidak's test. *P<0.001, **P<0.0001, IgG-Y vs IgG-O; $P<0.05, $$$$$P<0.0001, anti-CXCL13-Y vs IgG-O; ####P<0.0001, anti-CXCL13-0 vs IgG-O. FIG. 5G: Sensory responses measured by the latency to the touch of an adhesive tape placed on the hind paw after a unilateral sciatic nerve crush in aged mice treated with control IgG or anti-CXCL13 antibody (N=10, two-way ANOVA with post-hoc Sidak's test.P<0.01. FIG. 5H: Sensory responses measured by the latency to the removal of an adhesive tape placed on the hind paw after a unilateral sciatic nerve crush in aged mice treated with control IgG or anti-CXCL13 antibody (N=10, two-way ANOVA with post-hoc Sidak's test. P<0.01). FIG. 5I: Sensory responses measured by the latency to the touch of an adhesive tape placed on the hind paw after a unilateral sciatic nerve crush in aged mice treated with control IgG or anti-CXCL13 antibody (N=10, two-way ANOVA with post-hoc Sidak's test. <0.01. FIG. 5J: Sensory responses measured by the latency to the removal of an adhesive tape placed on the hind paw after a unilateral sciatic nerve crush in aged mice treated with control IgG or anti-CXCL13 antibody (N=10, two-way ANOVA with post-hoc Sidak's test. **<0.01. FIG. 5K: PGP9.5 immunostaining counterstained with DAPI shows the epidermal innervation of the hindpaw interdigital skin 18 days after a sciatic nerve crush. The dashed lines indicate the boundary of epidermis and dermis. Scale bar: 500 µm. FIG. 5L: Quantification of the number of intra-epidermal nerve fibers (IENF) per mm of interdigital kin following IgG or anti-CXCL13 antibody (N=6, one-way ANOVA with post-hoc Tukey's test. *$P<0.5$, $P<0.01$, **$P<0.0001$).

DETAILED DESCRIPTION

I. Definitions

The term "a" or "an" entity refers to one or more of that entity; for example, "an anti-CXCL13 antibody" is understood to represent one or more anti-CXCL13 antibodies. As such, the terms "a" (or "an"), "one or more," and "at least one" can be used interchangeably herein. Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "neuroregeneration" refers to the regrowth or repair of nervous tissues, cells or cell products. Such mechanisms can include generation of new neurons, glia, axons, myelin, or synapses. Neuroregeneration differs between the peripheral nervous system (PNS) and the central nervous system (CNS) by the functional mechanisms involved, especially in the extent and speed of repair. The processes that occur in peripheral regeneration can be divided into the following major events: Wallerian degeneration, axon regeneration/growth, and nerve reinnervation. When an axon is damaged, the distal segment undergoes Wallerian degeneration, losing its myelin sheath. The proximal segment can either die by apoptosis or undergo a chromatolytic reaction, i.e., the dissolution and breaking up of chromophil material (such as chromatin) of a nerve cell, which is an attempt at repair. The events that occur in peripheral regeneration occur with respect to the axis of the nerve injury. The proximal stump refers to the end of the injured neuron that is still attached to the neuron cell body; it is the part that regenerates. The distal stump refers to the end of the injured neuron that is still attached to the end of the axon; it is the part of the neuron that will degenerate but that remains in the area toward which the regenerating axon grows.

As used herein, the term "peripheral nerve" refers to one of the several nerves that branch off from the spinal cord and extend to all parts of the body. Unlike in the central nervous system, neuroregeneration in the peripheral nervous system is more common.

As used herein, the term "peripheral nerve injury" refers to an injury to one or more of the 43 pairs of motor and sensory nerves of the peripheral nervous system that connect the brain and spinal cord (the central nervous system) to the entire human body. Injuries to a peripheral nerve commonly are caused by lacerations (a cut or tear in the nerve tissue); severe bruising (contusion); injury during surgery on surrounding tissue; stretching (traction); drug injection injury; and electrical injury. Symptoms of peripheral nerve injury vary depending on the type of nerves-motor, sensory, or autonomic—that are damaged. Motor nerves control the movement of all muscles under conscious control, such as those used for walking, grasping things, or talking. Sensory nerves transmit information such as the feeling of a light touch, temperature, or the pain from a cut. Autonomic nerves control organs to regulate activities that animals do not control consciously, such as breathing, digesting food, and heart and gland functions. The peripheral nerves control the functions of sensation, movement and motor coordination. They are fragile and can be damaged easily. Nonlimiting examples of common peripheral nerve injuries include injuries of the brachial plexus, sciatic nerve, peroneal nerve and spinal accessory nerve.

The term "sciatic nerve" refers to a major peripheral nerve in humans and other vertebrate animals which begins in the lower part of the sacral plexus and runs through the hip joint and down the lower limbs. The sciatic nerve is also referred to as the ischiadic or ischiadic nerve. It is the longest and widest single nerve in the human body, going from the top of the leg to the foot on the posterior aspect.

The terms "sciatic nerve injury" refers to damage of the sciatic nerve including injuries due to trauma (e.g., pressure, stretching or cutting) to the nerve. This type of injury can cause degrees of muscle power loss and altered sensation. The causes of sciatic nerve injury can also be can be spinal or non-spinal or iatrogenic, including but not limited to spinal stenosis (due to degenerative bone disorders, trauma, inflammatory disease); spondylolisthesis; growth in the spinal canal (e.g., an abscess); non-spinal causes which compress or damage the nerve, e.g., due to piriformis syndrome, pregnancy, lumbar radiculopathy, trauma to the leg, pelvic or sciatic nerve tumors, or can be caused by medical examination, manipulation or treatment.

The term "spinal accessory nerve injury" refers to damage to the spinal accessory nerve, which is the 11th of 12 cranial nerves, which originate in the brain. The spinal accessory nerve allows two sets of muscles in the neck to function: the sternomastoid muscles, which allow the head to tilt and rotate, and the trapezius muscles, which allow for several motions, such as shrugging the shoulder or moving the shoulder blades. The spinal accessory nerve can be damaged during trauma or during surgery when surgeons are operating on lymph nodes or on the jugular vein in the neck. The symptoms are shoulder pain, outward "winging" of the shoulder blades, and weakness or atrophy of the trapezius muscle.

The term "brachial plexus injury" refers to an injury of the brachial plexus which is the network of nerves that sends signals from the spinal cord to the shoulder, arm and hand. A brachial plexus injury occurs when these nerves are stretched, compressed, or in the most serious cases, ripped apart or torn away from the spinal cord. Symptoms of more-severe injuries can include weakness or inability to use certain muscles in the hand, arm or shoulder, a complete lack of movement and feeling in the arm, including the shoulder and hand, and severe pain. Common causes of brachial plexus injuries include contact sports injuries, difficult birth, trauma, and tumors and/or chemotherapy.

The term "peroneal nerve" refers to the common peroneal nerve which branches from the sciatic nerve and provides sensation to the front and sides of the legs and top of the feet. This nerve also controls the muscles in the leg that lift the ankle and toes upward. Injuries to the peroneal nerve can cause numbness, tingling, pain, weakness and a gait problem called foot drop. The peroneal nerve can be injured by trauma and nerve compression, including knee dislocation, knee or leg fracture, knee or hip replacement surgery, compression of the peroneal nerve in the leg, and compression of the peroneal nerve by a nerve sheath tumor or nerve cyst.

As used herein, the term "dorsal root ganglion" (DRG) refers to an enlargement of the dorsal root of spinal nerves representing the cell bodies of the primary somatosensory neurons. The DRG are responsible for sensory function; they carry neural signals to the central nervous system (spinal cord, brain) from the peripheral nervous system. The DRG itself is a nodule containing spinal nerve cells. The cell bodies of sensory neurons known as first-order neurons are located in the dorsal root ganglia.

The term "therapeutically effective amount" refers to an amount of an antibody, polypeptide, polynucleotide, small organic molecule, or other drug effective to "treat" a condition or disorder in a subject or mammal. In the case of peripheral nerve damage or injury, such as sciatic nerve injury, the therapeutically effective amount of the drug can promote axonal regeneration of sensory neurons, epidermal innervation, and functional recovery of neurons following nerve injury in a subject that has nerve regenerative decline by increasing, for instance, the proliferation, differentiation, migration and/or survival of neural stem/precursor cells; reduce, retard or stop a decrease in neural cells; inhibit, e.g., suppress, retard, prevent, stop, or reverse a reduction in neural cells; increase the number, density and/or concentration of neural cells; change in the morphology or function of neural cells; or a change in the interactions among neural cells; relieve to some extent one or more of the symptoms associated with nerve injury, e.g., pain; improve quality of life; or a combination of such effects.

Terms such as "treating" or "treatment" or "to treat" or "alleviating" or "to alleviate" refer to both 1) therapeutic measures that cure, slow down, lessen symptoms of, reverse, and/or halt progression of a diagnosed pathologic condition of the injured nerve and 2) prophylactic or preventative measures that prevent and/or slow the regeneration of a peripheral nerve. Thus, those in need of treatment include those already with a peripheral nerve injury; and those prone to experience a peripheral nerve injury (e.g., sciatic nerve injury). Beneficial or desired clinical results include, but are not limited to, alleviation of symptoms, diminishment of extent of injured nerve tissue, stabilized (i.e., not worsening) state of the nerve injury, delay or slowing of injury progression, amelioration or palliation of the nerve damage, and regeneration of the injured nerve (whether partial or total), whether detectable or undetectable. Those in need of treatment include those already with a peripheral nerve injury or suspected of having a peripheral nerve injury as well as those prone to have a peripheral nerve injury, e.g., sciatica, or those in which the condition or injury or further injury is to be prevented. In particular, those in need of treatment include animals experiencing age-dependent decline in nerve regeneration functions.

By "subject" or "individual" or "animal" or "patient" or "mammal," is meant any subject, particularly a mammalian subject, for whom therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-CXCL13 antibody" and "an animal in need of treatment" includes subjects, such as mammalian subjects, that would benefit from administration of an anti-CXCL13 antibody or other CXCL13 binding molecule used, e.g., for detection of the level of CXCL13 polypeptide (e.g., for a diagnostic procedure) and/or from treatment, i.e., palliation or prevention of a pathologic condition affecting a peripheral nerve, with an anti-CXCL13 antibody or other CXCL13 binding molecule. Such subjects include animals that experience an aging-dependent decline in the naturally occurring nerve regenerative processes that promote neurological recovery following nerve injury.

As used herein, the term "aging-dependent regenerative decline" or "aging-dependent axonal regenerative decline" refers to a naturally occurring condition in animals associated with the aging process in which the axonal regenerative ability and axonal repair processes decline with aging. Whether a subject is affected by aging-dependent regenerative decline can be assessed by a medical professional by determining the age, overall health of the subject, observations of degree and length of time required for nerve damage repair, and the like. A subject with aging-dependent regenerative decline can be any chronological age, depending on that subject's other physiological or genetic traits. Any such subject would benefit from treatment as described herein for peripheral nerve injury.

A "binding molecule" or "antigen binding molecule" of the present disclosure refers in its broadest sense to a molecule that specifically binds an antigenic determinant. In one embodiment, the binding molecule specifically binds to CXCL13 (also called BCA-1). In another embodiment, a binding molecule of the disclosure is an antibody or an antigen binding fragment thereof, e.g., an anti-CXCL13 antibody. In another embodiment, a binding molecule of the disclosure comprises at least one heavy or light chain CDR of an antibody molecule. In another embodiment, a binding molecule of the disclosure comprises at least two CDRs from one or more antibody molecules. In another embodiment, a binding molecule of the disclosure comprises at least three CDRs from one or more antibody molecules. In another embodiment, a binding molecule of the disclosure comprises at least four CDRs from one or more antibody molecules. In another embodiment, a binding molecule of the disclosure comprises at least five CDRs from one or more antibody molecules. In another embodiment, a binding molecule of the disclosure comprises at least six CDRs from one or more antibody molecules. In certain embodiments, one or more of the CDRs is from MAb 5261, MAb 5378, MAb 5080, MAb 1476, 3D2, 3C9, MAb 1758, MAb 5091, or MAb 0745. Exemplary anti-CXCL13 antibodies are disclosed, for example in U.S. Pat. No. 9,963,504, which is incorporated herein by reference in its entirety.

"Inhibits" as used herein can include partial or complete blocking of, e.g., binding, activity, function, interaction, or other measurable feature.

The present disclosure is directed to a method of promoting axonal regeneration of sensory neurons, epidermal innervation and/or functional recovery of neurons following peripheral nerve injury in a subject experiencing aging-dependent nerve regenerative decline, e.g., an elderly subject or a subject so diagnosed by a healthcare provider, comprising administering to the subject an anti-CXCL13 binding molecule, e.g., an antibody, or antigen-binding fragment thereof, variant, or derivative thereof. Unless specifically referring to full-sized antibodies such as naturally occurring antibodies, the term "anti-CXCL13 antibody" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain (s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a CXCL13 polypeptide or fragment or variant thereof. Standard techniques known to those of skill in the art can be used to introduce mutations in the nucleotide sequence encoding a human anti-CXCL13 antibody, including, but not limited to, site-directed mutagenesis and PCR-mediated mutagenesis which result in amino acid substitutions. In certain embodiments the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a CXCL13 polypeptide, e.g., human, murine, or both human and murineCXCL13). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, (.gamma., .mu., .alpha., .delta., .epsilon.) with some subclasses among them (e.g., .gamma.1-.gamma.4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (K, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three-dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule can consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three-dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the j-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

Numbering of all CDR definitions in Table 1 is according to the numbering conventions set forth by Kabat et al. (see below).

TABLE 1

[1]Numbering of all CDR definitions in Table 1 is according to the numbering conventions set forth by Kabat et al. (see below).

| i. | CDR Definitions[1] | |
|---|---|---|
| ii. | Kabat | Chothia |
| 2. VHCDR1 | 31–35 | 26–32 |
| 3. VHCDR2 | 50–65 | 52–58 |
| 4. VHCDR3 | 95–102 | 95–102 |
| 5. VLCDR1 | 24–34 | 26–32 |
| 6. VLCDR2 | 50–56 | 50–52 |
| 7. VLCDR3 | 89–97 | 91–96 |

Antibody variable domains can also be analyzed, e.g., using the IMGT information system (www://imgt.cines.fr/) (IMGT®/V-Quest) to identify variable region segments, including CDRs. (See, e.g., Brochet et al., Nucl. Acids Res., 36:W503-508, 2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-CXCL13 antibody or antigen-binding fragment, variant, or derivative thereof of the present disclosure are according to the Kabat numbering system.

Antibodies or antigen-binding fragments, variants, or derivatives thereof of the disclosure include, but are not limited to, polyclonal, monoclonal, multispecific, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-CXCL13 antibodies disclosed herein). ScFv molecules are known in the art and are described, e.g., in U.S. Pat. No. 5,892,019. Immunoglobulin or antibody molecules of the disclosure can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the disclosure can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, a binding polypeptide for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

In certain anti-CXCL13 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the disclosure are not identical. For example, each monomer can comprise a different target binding site, forming, for example, a bispecific antibody.

The heavy chain portions of a binding molecule for use in the methods disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. In some embodiments the light chain portion comprises at least one of a VL or CL domain.

CXCL13 is a small chemokine which belongs to the CXC chemokine family. It is selectively chemotactic for B cells belonging to both the B-1 and B-2 subsets, and elicits its effects by interacting with chemokine receptor CXCR5. (Legler D F, Loetscher M, Roos R S, Clark-Lewis I, Baggiolini M, Moser B (February 1998). *J. Exp. Med.* 187 (4): 655-60; Ansel K M, Harris R B, Cyster J G (January 2002). *Immunity.* 16 (1): 67-76). CXCL13 and its receptor CXCR5 control the organization of B cells within follicles of lymphoid tissues (Ansel K M, Ngo V N, Hyman P L, Luther S A, Förster R, Sedgwick J D, Browning J L, Lipp M, Cyster J G (July 2000. *Nature.* 406 (6793): 309-14) CXCL13 is expressed highly in the liver, spleen, lymph nodes, and gut of humans. (Legler D F, Loetscher M, Roos R S, Clark-Lewis I, Baggiolini M, Moser B (February 1998). *J. Exp. Med.* 187 (4): 655-60). As described herein, CXCL13 can, in certain instances, also be chemotactic for CXCR5-expressing T lymphocytes, especially CD8+T-lymphocytes.

Anti-CXCL13 antibodies, or antigen-binding fragments, variants, or derivatives thereof disclosed herein can be described or specified in terms of the epitope(s) or portion(s) of an antigen, e.g., a target polypeptide disclosed herein (e.g., CXCL13) that they recognize or specifically bind. The portion of a target polypeptide that specifically interacts with the antigen binding domain of an antibody is an "epitope" or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain at least seven, at least nine, or between at least about 15 to about 30 amino acids. Since a CDR can recognize an antigenic peptide or polypeptide in its tertiary form, the amino acids comprising an epitope need not be contiguous, and in some cases, are not even on the same peptide chain. A peptide or polypeptide epitope recognized by anti-CXCL13 antibodies of the present disclosure can contain a sequence of at least 4, at least 5, at least 6, at least 7, at least 8, at least 9, at least 10, at least 15, at least 20, at least 25, or between about 15 to about 30 contiguous or non-contiguous amino acids of CXCL13.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" can have a higher specificity for a given epitope than antibody "B," or antibody "A" can bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody can cross-react with the related epitope.

By way of non-limiting example, an antibody binds a first epitope preferentially if it binds said first epitope with a dissociation constant ($K_D$) that is less than the antibody's $K_D$ for the second epitope. In another non-limiting example, an antibody binds a first antigen preferentially if it binds the first epitope with an affinity that is at least one order of magnitude less than the antibody's $K_D$ for the second epitope. In another non-limiting example, an antibody binds a first epitope preferentially if it binds the first epitope with an affinity that is at least two orders of magnitude less than the antibody's $K_D$ for the second epitope.

In another non-limiting example, an antibody binds a first epitope preferentially if it binds the first epitope with an off rate (k(off)) that is less than the antibody's k(off) for the second epitope. In another non-limiting example, an antibody binds a first epitope preferentially if it binds the first epitope with an affinity that is at least one order of magnitude less than the antibody's k(off) for the second epitope. In another non-limiting example, an antibody binds a first epitope preferentially if it binds the first epitope with an affinity that is at least two orders of magnitude less than the antibody's k(off) for the second epitope. An antibody or antigen-binding fragment, variant, or derivative disclosed herein binds a target polypeptide disclosed herein (e.g., CXCL13, e.g., human, murine, or both human and murine-CXCL13) or a fragment or variant thereof with an off rate (k(off)) of less than or equal to $5 \times 10^{-2}$ $sec^{-1}$, $10^{-2}$ $sec^{-1}$, $5 \times 10^{-3}$ $sec^{-1}$ or $10^{-3}$ $sec^{-1}$. In some embodiments an antibody of the disclosure can be said to bind a target polypeptide disclosed herein (e.g., CXCL13, e.g., human, murine, or both human and murine CXCL13) or a fragment or variant thereof with an off rate (k(off)) less than or equal to $5 \times 10^{-4}$ $sec^{-1}$, $10^{-4}$ $sec^{-1}$, $5 \times 10^{-5}$ $sec^{-1}$, or $10^{-5}$ $sec^{-1}$, $5 \times 10^{-6}$ sec-1, $10^{-6}$ $sec^{-1}$, $5 \times 10^{-7}$ $sec^{-1}$ or $10^{-7}$ $sec^{-1}$.

In certain embodiments, an antibody or antigen-binding fragment, variant, or derivative disclosed herein binds a target polypeptide disclosed herein (e.g., CXCL13, e.g., human, murine, or both human and murine CXCL13) or a fragment or variant thereof with an on rate (k(on)) of greater than or equal to $10^3$ $M^{-1}$ $sec^{-1}$, $5 \times 10^3$ $M^{-1}$ $sec^{-1}$, $10^4$ $M^{-1}$ $sec^{-1}$ or $5 \times 10^4$ $M^{-1}$ $sec^{-1}$. In some embodiments an antibody of the disclosure binds a target polypeptide disclosed herein (e.g., CXCL13, e.g., human, murine, or both human and murine CXCL13) or a fragment or variant thereof with an on rate (k(on)) greater than or equal to $10^5$ $M^{-1}$ sec-1, $5 \times 10^5$ $M^{-1}$ $sec^{-1}$, $10^6$ $M^{-1}$ $sec^{-1}$, or $5 \times 10^6$ $M^{-1}$ $sec^{-1}$ or $10^7$ $M^{-1}$ $sec^{-1}$.

An antibody is said to competitively inhibit binding of a reference antibody to a given epitope if it preferentially binds to that epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-CXCL13 antibodies or antigen-binding fragments, variants, or derivatives thereof of the disclosure can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross-reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

Anti-CXCL13 binding molecules, e.g., antibodies or antigen-binding fragments, variants or derivatives thereof, of the disclosure can also be described or specified in terms of their binding affinity to a polypeptide of the disclosure, e.g., CXCL13, e.g., human, murine, or both human and murine CXCL13. Exemplary binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-13}$ M, $10^{-13}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In one embodiment, the anti-CXCL13 binding molecule, e.g., an antibody or antigen binding fragment thereof of the disclosure binds human CXCL13 with a Kd of less than about $5\times10^{-9}$ M to about $5\times10^{-10}$ M, e.g., wherein the antibody is MAb 5261 and the Kd is less than or equal to about $5\times10^{-9}$ M. In another embodiment, the anti-CXCL13 binding molecule, e.g., an antibody or antigen binding fragment thereof, of the disclosure binds murine CXCL13 with a Kd of less than about $5\times10^{-7}$ M to about $9\times10^{-9}$ M, e.g., wherein the antibody is MAb 5261 and the Kd is less than or equal to about $8\times10^{-9}$ M. See, e.g., U.S. Pat. No. 9,963,504.

As used herein, the term "chimeric antibody" will be held to mean any antibody wherein the immunoreactive region or site is obtained or derived from a first species and the constant region (which can be intact, partial or modified in accordance with the instant disclosure) is obtained from a second species. In some embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class, for example, from an antibody from a different species. An engineered antibody in which one or more "donor" CDRs from a non-human antibody of known specificity is grafted into a human heavy or light chain framework region is referred to herein as a "humanized antibody." In certain embodiments it is not necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody can comprise solely residues of human origin, in which case these framework regions of the humanized antibody are referred to as "fully human framework regions." Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the CXCL13 antigen. A human framework region that has been engineered in this manner would thus comprise a mixture of human and donor framework residues, and is referred to herein as a "partially human framework region."

For example, humanization of an anti-CXCL13 antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-CXCL13 antibody. See also U.S. Pat. Nos. 5,225,539; 5,585,089; 5,693,761; 5,693,762; 5,859,205; herein incorporated by reference. The resulting humanized anti-CXCL13 antibody would comprise at least one rodent or mutant rodent CDR within the fully human framework regions of the variable domain of the heavy and/or light chain of the humanized antibody. In some instances, residues within the framework regions of one or more variable domains of the humanized anti-CXCL13 antibody are replaced by corresponding non-human (for example, rodent) residues (see, for example, U.S. Pat. Nos. 5,585,089; 5,693,761; 5,693,762; and 6,180,370), in which case the resulting humanized anti-CXCL13 antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies can include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

II. Target Polypeptide Description

CXCL13 is a small chemokine that is shown herein to promote the migration of B lymphocytes (and a subset of T cells) (FIGS. 2A, 2B and 5D), apparently by stimulating calcium influx into, and chemotaxis of, cells expressing Burkitt's lymphoma receptor 1 (BLR-1). It can therefore function in the homing of B lymphocytes to follicles.

As used herein, the terms "CXCL13" and "CXCL13 polypeptide" are used interchangeably. In certain embodiments, CXCL13 can include a full-sized CXCL13 polypeptide or a fragment thereof, or a CXCL13 variant polypeptide, wherein the fragment of CXCL13 or CXCL13 variant polypeptide retains some or all functional properties of the full-sized CXCL13. The human CXCL13 polypeptide and polynucleotide sequences (SEQ ID NOs: 1 and 2, respectively) have been described, see, e.g., Legler, et. al., J. Exp. Med. 187(4):655-660 (1998). The mouse CXCL13 polypeptide and polynucleotide sequences (SEQ ID NOs: 3 and 4, respectively) have been described, see, e.g., Gunn, et. al., Nature 391(6669):799-803 (1998)). Furthermore, the cynomolgus monkey CXCL13 polypeptide sequence has been described as shown in SEQ ID NO: 5.

III. Axonal Regeneration

In young mammals, axons readily regenerate after peripheral nerve injury. The distal portion of the axon, which is disconnected from the cell body, undergoes Wallerian degeneration. This active process results in fragmentation and disintegration of the axon. Debris is removed by glial cells, e.g., Schwann cells, and macrophages. Proximal axons can then regenerate and re-innervate their targets, allowing recovery of function. However, the axonal repair processes and the ability to regenerate axons declines with the aging process. Aging deeply influences several morphologic and functional features of the peripheral nervous system (PNS). After injury, Wallerian degeneration is delayed in aged animals, with myelin remnants accumulated in the macrophages being larger than in young animals. The interaction between Schwann cells and regenerative axons takes longer, and the amount of trophic and tropic factors secreted by reactive Schwann cells and target organs are lower in older subjects than they are in younger subjects. The rate of axonal regeneration becomes slower and the density of regenerating axons decreases in aged animals. Aging also determines a reduction in terminal and collateral sprouting of regenerated fibers, further limiting the capabilities for target reinnervation and functional restitution. These age-related changes are not linearly progressive with age; the capabilities for axonal regeneration and reinnervation are maintained throughout life, but tend to be delayed and less effective with aging. (E Verdú, et al., J Peripher. Nerv Syst. 2000 December; 5(4):191-208; Fenrich K. et al, Can J Neurol Sci. 2004 May; 31(2):142-56). These observations suggest that aging leads to development of unique molecular and cellular mechanisms that, when combined with injury-specific cellular signals, primes neurons towards regenerative failure.

To test this hypothesis, the inventors conducted RNAseq experiments in sciatic dorsal root ganglia (DRG), which showed an aging-dependent enrichment in immune and cytokine/chemokine signaling pathways both before and following a sciatic nerve injury. The primary age-associated molecular signature was represented by an increase in T cell activation and signaling. Mechanistically, it was found that an aging-dependent increase in inflammatory cytokines including lymphotoxin activates $NF_{\kappa}B$ (nuclear factor kappa-light-chain-enhancer of activated B cells) in DRG, which upregulates the chemokine CXCL13, which in turn recruits CXCR5+CD8+ T cells in proximity of neurons that act as antigen presenting cells (APC) by expressing MHC-I. Activated CD8' T cells in turn repress axonal regeneration of sensory DRG neurons by inhibiting regenerative signals via caspase 3-dependent reduction in pAKT and pS6. Surprisingly, in vivo antibody-mediated specific CD8+ T cell depletion or CXCL13 neutralization were shown to restore axonal regeneration of sensory neurons to the level of the young and beyond, promoting functional recovery. These results indicate that there is a unique mechanism that restricts the axonal regenerative ability in older subjects and show that antibody-mediated manipulation of neuron-immune cell communication can be used clinically to counteract the regenerative decline observed in older subjects and promote repair following injury of peripheral nerves, e.g., sciatic nerve injury.

IV. Anti-CXCL13 Antibodies

Antibodies that bind CXCL13 have been described in the art. See, for example U.S. Pat. No. 9,963,504, incorporated herein in its entirety by reference. Commercial antibodies that bind CXCL13 also have been disclosed in the art, e.g., rat anti-mouse MAb 470 (R & D Systems) and mouse anti-human MAb 801 (R & D Systems). Other anti-CXCL13 binding molecules are disclosed, e.g., in US Patent Application Publications US2008/0227704 and US2008/0199481, and in PCT Publication No. WO2020057540A1.

The antibodies of the disclosure comprise anti-CXCL13 antibodies or antigen-binding fragments, variants, or derivatives thereof that bind to CXCL13, e.g., MAb 5261 (human), MAb 5378 (VH and VL of Mab 5261 with murine constant regions), MAb 5080 (humanized parent antibody of Mab 5261), MAb 1476 (chimeric antibody with the VH and VL of 3D2, with human constant regions), 3D2 (parent murine monoclonal antibody of 5261 and 5080), MAb 5091 (human), 3C9 (murine monoclonal antibody), MAb 1758 (humanized 3C9), or MAb 0745 (3C9 hybridoma). In certain embodiments the anti-CXCL13 antibodies bind human, primate, murine, or both human and murine CXCL13. In certain embodiments, the anti-CXCL13 antibodies of the disclosure are humanized. In other embodiments, the anti-CXCL13 antibodies block CXCL13 binding to its receptor, e.g., CXCR5. In certain embodiments, the anti-CXCL13 antibodies of the disclosure are MAb 5261, MAb 5378, MAb 5080, MAb 1476, 3D2, 3C9, MAb 1758, MAb 0745, MAb 5091 or antigen-binding fragments, variants, or derivatives thereof.

The disclosure generally relates to a method of promoting axonal regeneration of sensory neurons, epidermal innervation and functional recovery of said neurons following peripheral nerve injury in a subject experiencing age-dependent nerve regenerative decline. The method comprises administering to the subject an effective amount of an isolated binding molecule which specifically binds to CXCL13, or an antigen-binding fragment, variant, or derivative thereof. In certain embodiments, the antibody blocks the interaction of CXCL13 with its receptor, CXCR5. Antibodies having these properties can be used in the methods provided herein. Antibodies that can be used include, but are not limited to MAbs MAb 5261, MAb 5378, MAb 5080, MAb 1476, MAb 3D2, MAb 3C9, MAb 0745, MAb 5091, or MAb 1758 which are fully described in U.S. Pat. No. 9,963,504 and incorporated herein by reference.

In certain embodiments an anti-CXCL13 antibody for use in the methods provided herein binds human, or murine, or both human and murine CXCL13. Also useful are antibodies which bind to the same epitope as any of the aforementioned antibodies and/or antibodies which competitively inhibit any of the aforementioned antibodies. In certain embodiments, the antigen binding molecule specifically binds to the same CXCL13 epitope as MAb 5261 and MAb 5378. Amino acid sequence of the MAb 5261, MAb 5378, MAb 5080, MAb 1476, MAb 3D2, MAb 3C9, MAb 745, MAb 5091, and MAb 1758 variable heavy chains and variable light chains are shown in Table 2 below. The complementarity determining regions (CDRs) are underlined. The CDR sequences are also shown in Table 3 below.

TABLE 2

CXCL13 Antibody Variable Domains

| Antibody | SEQ ID NO. | VH | SEQ ID NO. | VL |
|---|---|---|---|---|
| 3D2 and 1476 | 6 | EVQLQESGPGILQPSQTLNL TCSFSGFSLS<u>TFGMGVGW</u>IR QPSGKGLEWLA<u>HIWWDDD RRYNPALKS</u>RLTISKETSKN QVFLKIANVDTADTATYYC TR<u>IAGYYGSRDWFAY</u>WGQ GTTVTVSS (H1609) | 7 | DIVLTQSPASLAVSLGQRATI SC<u>RASESVDNSGISFMH</u>WYQ QKPGQPPKLLIF<u>RASDLES</u>GI PARFSGSGSRTDFLTVNPV ETDDVATYFC<u>QQSNKDPWT</u> FGGGTKLEIK (L0293) |
| 5080 | 8 | QVQLQESGPGLVKPSETLSL TCTVSGFSLS<u>TFGMGVGW</u>I RQPPGKGLEWIA<u>HIWWDD DRRYNPALKS</u>RVTISKDTSK NQFSLKLSSVTAADTAVYY CAR<u>IAGYYGSRDWFAY</u>WG QGTTVTVSS (H2177) | 9 | DIQMTQSPSSLSASVGDRVTI TC<u>RASESVDNSGISFMH</u>WYQ QKPGKAPKLLIF<u>RASDLES</u>G VPSGFSGSGSRTDFLTISSL QPEDFATYYC<u>QQSNKDPWT</u> FGQGTKLEIK (L5055) |
| 5261 and 5378 | 10 | QVQLQESGPGLVKPSETLSL TCTVSGFSLS<u>TFGMGVGW</u>I RQPPGKGLEWIA<u>HIWWDD DRRYNPALKS</u>RVTISKDTSK NQFSLKLSSVTAADTAVYY CAR<u>IAGYYGSRDWFAY</u>WG QGTTVTVSS (H2177) | 11 | DIQMTQSPSSLSASVGDRVTI TC<u>RASESVDNMGISFMH</u>WY QQKPGKAPKLLIF<u>RASDLES</u> GVPSRFSGSGSGTDFTLTISS LQPEDFATYYC<u>QQSNKDPW</u> <u>T</u>FGQGTKLEIK (L5140) |
| 3C9 and 745 | 12 | QVQLKESGPGILQPSQTLSL TCSFSGFSLS<u>TFNMGVGW</u>IR RPSGKGLEWL<u>THIWWDDD KY</u>YNPALRNRLTISKDTSK NQVFLKIANVDTADTATYY CAR<u>RLGQYDYDEGFDY</u>WG QGTTVTVSS (H1298) | 13 | DVLMTQTPLSLPVSLGDQAS ISC<u>RSSQSLVHSNGNTYLH</u>W YLQKPGQSPKLLIF<u>KVSNRFS</u> GVPDRFSGSGSGTDFLKISR VEAEDLGVYFC<u>SQSTHVPYT</u> FGGGTKLEIK (L0294) |
| 5091 | 14 | QITLKESGPTLVKPTQTLTL TCTFSGFSLS<u>TFGATVGW</u>IR QPPGKALEWL<u>ALIYWDDD KR</u>YNPSLRSRLTITKDTSKN QVVLTMTNMDPVDTATYY CAR<u>RLGQYDYDEGFDY</u>WG QGTTVTVSS (H5015) | 15 | DVVMTQTPLSLPVTPGEPASI SC<u>RSSQSLLDSYNGNTYLA</u>W YLRKPGQSPQLLIY<u>RLSYRA</u> SGVPDRFSGSGSGTDFLKIS RVEAEDVGVYYC<u>SQSTHVP</u> <u>YT</u>FGQGTKLEIK (L542) |
| 1758 | 16 | QVTLKESGPALVKPTQTLTL TCTFSGFSLS<u>TFNMGVGW</u>IR QPPGKALEWL<u>THIWWDDD KY</u>YNPALRNRLTISKDTSK NQVVLTMTNMDPVDTATY YCAR<u>RLGQYDYDEGFDY</u>W GQGTLVTVSS (H1688) | 17 | DIQMTQSPSSLSASVGDRVTI TC<u>RSSQSLVHSNGNTYLH</u>W YQQKPGKAPK<u>LLIFKVSNRF</u> SGVPSRFSGSGSGTDFLTIS SLQPEDFATYYC<u>SQSTHVPY</u> <u>T</u>FGQGTKLEIK (L0444) |

TABLE 3

| Clone ID | CDR | Sequence | SEQ ID NO |
|---|---|---|---|
| H1609 and H2177 | HCDR1 | TFGMGVG | 18 |
| H1298 and H1688 | HCDR1A | STFNMGVG | 19 |
| H5015 | HCDR1B | STFGATVG | 20 |
| H1609 and H2177 | HCDR2 | HIWWDDDRRYNPALKS | 21 |
| H1298 and H1688 | HCDR2A | WLTHIWWDDDKY | 22 |
| H5015 | HCDR2B | WLALIYWDDDKR | 23 |
| H1609 and 2177 | HCDR3 | IAGYYGSRDWFAY | 24 |
| H1298, H1688 and H5015 | HCDR3A | ARRLGQYDYDEGFD | 25 |
| L0293 and L5055 | LCDR1 | RASESVDNSGISFMH | 26 |
| L5140 | LCDR1A | RASESVDNMGISFMH | 27 |
| L0294 and L0444 | LCDR1B | HSNGNTYLHWY | 28 |
| L542 | LCDR1C | DSYNGNTYLAWY | 29 |
| L2093, L5055, and L5140 | LCDR2 | RASDLES | 30 |
| L2094 and L0444 | LCDR2A | LLIFKVSNRF | 31 |
| L542 | LCDR2B | LLIYRLSYRA | 32 |
| L2093, L5055, and L5140 | LCDR3 | QQSNKDPWT | 33 |
| L2094, L0444, and L542 | LCDR3A | SQSTHVPY | 34 |

In one embodiment, the present disclosure provides an isolated binding molecule, e.g., an antibody or antigen binding fragments, variants, and derivatives thereof, which specifically binds to the same CXCL13 epitope as a reference antibody, e.g., MAb 5261, MAb 5378, MAb 5080, MAb 1476, MAb 5091, MAb 1758, 3D2, or 3C9. In another embodiment, the present disclosure provides an isolated binding molecule, e.g., an antibody or antigen binding fragment thereof, which specifically binds to CXCL13, and competitively inhibits a reference antibody, e.g., MAb 5261, MAb 5378, MAb 5080, MAb 1476, MAb 5091, MAb 1758, 3D2, or 3C9, from specifically binding to CXCL13, e.g., human, primate, murine, or both human and murine CXCL13.

In certain embodiments, the binding molecule of the disclosure has an amino acid sequence that has at least about 80%, about 85%, about 88%, about 89%, about 90%, about 91%, about 92%, about 93%, about 94%, or about 95% sequence identity of an amino acid sequence for the reference anti-CXCL13 antibody molecule. In a further embodiment, the binding molecule shares at least about 96%, about 97%, about 98%, about 99%, or 100% sequence identity to a reference antibody. In certain embodiments, the reference antibody is MAb 5261, MAb 5378, MAb 5080, MAb 1476, MAb 5091, MAb 1758, 3D2, or 3C9.

In certain embodiments, the present disclosure provides an isolated antibody or antigen-binding fragment thereof comprising, consisting essentially of, or consisting of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 6, 8, 10, 12, 14, or 16.

In another embodiment, the present disclosure provides an isolated antibody or antigen-binding fragment thereof comprising, consisting essentially of or consisting of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 18, 19, 20, 21, 22, 23, 24, or 25.

In another embodiment, the present disclosure provides an isolated antibody or antigen-binding fragment thereof comprising, consisting essentially of, or consisting of an immunoglobulin heavy chain variable domain (VH domain), where the VH domain has an amino acid sequence that is at least about 80%, about 85%, about 90%, about 95%, about 96%, about 97%, about 98%, about 99%, or identical to SEQ ID NO: 6, 8, 10, 12, 14, or 16.

In another embodiment, the present disclosure provides an isolated antibody or antigen-binding fragment thereof comprising, consisting essentially of, or consisting of an immunoglobulin heavy chain variable domain (VH domain), where at least one of the CDRs of the VH domain has an amino acid sequence identical, except for 1, 2, 3, 4, or 5 conservative amino acid substitutions, to CDR1, CDR2 or CDR3 of SEQ ID NO:6, 8, 10, 12, 14, or 16

In another embodiment, the present disclosure provides an isolated antibody or antigen-binding fragment thereof comprising, consisting essentially of, or consisting of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 18, 19, 20, 21, 22, 23, 24, or 25.

In another embodiment, the present disclosure provides an isolated antibody or antigen-binding fragment thereof comprising, consisting essentially of, or consisting of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO:6, 8, 10, 12, 14, or 16, wherein an anti-CXCL 13 antibody comprising the encoded VH domain specifically or preferentially binds to CXCL13.

In another embodiment, the present disclosure provides an isolated antibody or antigen-binding fragment thereof comprising, consisting essentially of, or consisting of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 7, 9, 11, 13, 15, or 17.

In another embodiment, the present disclosure provides an isolated antibody or antigen-binding fragment thereof comprising, consisting essentially of, or consisting of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 26, 27, 28, 29, 30, 31, 32, 33, or 34.

In another embodiment, the present disclosure provides an isolated antibody or antigen-binding fragment thereof comprising, consisting essentially of, or consisting of an immunoglobulin light chain variable domain (VL domain), where the VL domain has an amino acid sequence that is at least about 80%, about 85%, about 90%, about 95%, about 96%, about 97%, about 98%, about 99%, or identical to SEQ ID NO:7, 9, 11, 13, 15, or 17.

In another embodiment, the present disclosure provides an isolated antibody or antigen-binding fragment thereof comprising, consisting essentially of, or consisting of an immunoglobulin light chain variable domain (VL domain), where at least one of the CDRs of the VL domain has an amino acid sequence identical, except for 1, 2, 3, 4, or 5 conservative amino acid substitutions, to CDR1, CDR2 or CDR3 of SEQ ID NO:7, 9, 11, 13, 15, or 17.

In another embodiment, the present disclosure provides an isolated antibody or antigen-binding fragment thereof comprising, consisting essentially of, or consisting of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 26, 27, 28, 29, 30, 31, 32, 33, or 34.

In a further embodiment, the present disclosure includes an isolated antibody or antigen-binding fragment thereof comprising, consisting essentially of, or consisting of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO:7, 9, 11, 13, 15, or 17, wherein an anti-CXCL13 antibody comprising the encoded VL domain specifically or preferentially binds to CXCL13.

Suitable biologically active variants of the anti-CXCL13 antibodies of the disclosure can be used in the methods of the present disclosure. Such variants will retain the desired binding properties of the parent anti-CXCL13 antibody. Methods for making antibody variants are generally available in the art.

V. Treatment Methods Using Therapeutic Anti-CXCL13 Antibodies

Lymphoid chemokine CXCL13 is expressed by follicular dendritic cells (FDCs) and macrophages. Through its receptor, CXCR5, which is found on a variety of immune cells (e.g., B cells, follicular helper T cells, and recently-activated T cells), CXCL13 induces intracellular changes necessary for maintenance of immune system homeostasis, lymphoid organogenesis, leukocyte trafficking and chemotactic migration as well as development of secondary lymphoid tissue (e.g. germinal centers). Overexpression of CXCL13 and its receptor CXCR5 have been implicated in a variety of autoimmune diseases (e.g., Multiple sclerosis (see, e.g., Corcione et al., PNAS 101(30):11064-11069 (2004); Serafini et al., Brain Pathol. 14:164-174 (2004); Magliozzi et al., Brain 130: 1089-1104 (2007)), arthritis (e.g., Rheumatoid arthritis (see, e.g., Rioja et al., Arthritis & Rheumatism 58(8):2257-2267 (2008); Shi et al., J. Immuno. 166: 650-655 (2001); Schmutz et al., Arthritis Restearch and Therapy 7:R217-R229 (2005); Hjelmstrom et al., J. Leukocyte Bio. 69:331-339 (2001)), chronic gastritis (see, e.g., Hjelmstrom et al.; Mazzucchelli et al., Brain 130:1089-1104 (2007)), gastric lymphomas (see, e.g., id.; Nobutani et al., FEMS Immunol Med Microbiol 60:156-164 (2010)), transplant rejection (see, e.g., Steinmetz et al., Kidney International 67:1616-1621 (2005)), Sjogren syndrome (SS) (see, e.g., Barone et al., J. Immuno. 180:5130-5140 (2008); Hjelmstrom et al.), Systemic Lupus Erythematosis (SLE) (see, e.g., Steinmetz et al., Lee et al., J. Rheum. 37(1):45-52 (2010); Schiffer et al., J. Immun. 171:489-497 (2003)), active mixed cryoglobulinemia (MC) vasculitis in Hepatitis C virus infection (see, e.g., Sansonno et al., Blood 112(5): 1620-1627 (2008)), Juvenile dermatomyositis (see, e.g., de Padilla et al., Arthritis & Rheumatism 60(4):1160-1172 (2009)), and Myasthenia Gravis (see, e.g., Matsumoto et al., J. Immuno. 176:5100-5107 (2006); Meraouna et al., Blood 108(2):432-440 (2006); Saito et al., J. Neuroimmunol 170: 172-178 (2005)) and certain cancers (e.g., Burkitt's lymphoma (see, e.g., Forster et al., Blood 84:830-840 (1994); Forster et al., Cell 87:1037-1047 (1996)), Non-Hodgkin Lymphoma (see, e.g., Trentin et al., Ann. Rev. Immunol. 6:251-81 (1988); Gong et al., J. Immunol. 174: 817-826 (2005); Hamaguchi et al., J. Immunol. 174:4389-4399 (2005)), Carcinoma (e.g., colon and pancreatic) (see, e.g., Gunther et al., Int. J. Cancer 116:726-733 (2005); Meijer et al., Cancer Res. 66: 9576-9582 (2006)), breast cancer (see, e.g., Panse et al., British Journal of Cancer 99:930-938 (2008)), Chronic lymphocytic leukemia (CLL) (see, e.g., Burkle et al., Blood 110:3316-3325 (2007)), and prostate cancer (see, e.g., Singh et al., Cancer Letters 283 (1):29-35 (2009)).

Heretofore, neuronal expression of CXCL13 has not been known to be associated with aging-dependent enrichment of T cell signaling pathways. The present disclosure demonstrates that the inflammatory cytokine lymphotoxin activates $NF_KB$, which induces the neuronal expression of CXCL13, which in turn recruits $CXCR5^+$ $CD8^+$ T cells in proximity of DRG neurons expressing MHC-1. CD8+ T cells are shown herein to repress axonal regeneration of sensory DRG neurons by inhibiting the regenerative signals pAKT and pS6 via caspase 3 activation. It is shown herein that neutralization with anti-CXCL13 binding molecules prevents CXCR5+CD8+ T cell recruitment to the DRG, thus reversing aging-dependent regenerative decline, and promoting neurobiological recovery following peripheral nerve injury, such as sciatic nerve injury.

Certain methods of the disclosure are directed to the use of anti-CXCL13 binding molecules, e.g., antibodies, including antigen-binding fragments, variants, and derivatives thereof, to promote peripheral nerve regeneration in a subject with aging-dependent axonal regeneration decline, following peripheral nerve injury such as sciatic nerve injury.

Although the following discussion refers to diagnostic methods and treatment of peripheral nerves to promote axonal regeneration with an anti-CXCL13 antibody of the disclosure, the methods described herein are also applicable to the antigen-binding fragments, variants, and derivatives of these anti-CXCL13 antibodies that retain the desired properties of the anti-CXCL13 antibodies of the disclosure, e.g., capable of specifically binding CXCL13, e.g., human, primate, or mouse, or human and mouse CXCL13, and having CXCL13 neutralizing activity, e.g., blocking CXCL13 from binding to CXCR5.

In one embodiment, treatment includes the application or administration of an anti-CXCL13 binding molecule, e.g., an antibody or antigen-binding fragment thereof, of the current disclosure to a patient, or application or administration of the anti-CXCL13 binding molecule to an isolated tissue or cell line from a patient, where the patient has or is suspected of having aging-dependent axonal regeneration decline and has or is suspected of having a peripheral nerve injury, damage, or a predisposition toward peripheral nerve injury, such as sciatic nerve injury. In another embodiment, treatment is also intended to include the application or administration of a pharmaceutical composition comprising the anti-CXCL13 binding molecule, e.g., an antibody or antigen binding fragment thereof, of the current disclosure to a patient, or application or administration of a pharmaceutical composition comprising the anti-CXCL13 binding molecule to an isolated tissue or cell line from a patient, who has, or is suspected of having aging-dependent axonal regeneration decline and has or is suspected of having a peripheral nerve injury, or a predisposition toward peripheral nerve injury, such as sciatic nerve injury.

The anti-CXCL13 binding molecules, e.g., antibodies or binding fragments thereof, of the present disclosure are useful for the treatment of peripheral nerve injuries or conditions requiring axonal regeneration. For example, therapy with at least one anti-CXCL13 antibody causes a physiological response that is beneficial with respect to axonal regeneration in a patient that has aging-dependent axonal regeneration decline.

In one embodiment, the disclosure relates to anti-CXCL13 binding molecules, e.g., antibodies or binding fragments thereof, according to the present disclosure for use as a medicament or the manufacture of a medicament, in particular for use in the treatment or prophylaxis of peripheral nerve injury, such as sciatic nerve injury. In certain embodiments, an anti-CXCL13 binding molecule, e.g., an antibody or antigen-binding fragment thereof, e.g., MAb 5261, MAb 5378, MAb 5080, MAb 1476, 3D2, or 3C9, of the disclosure is used to promote axonal regeneration in a patient with a peripheral nerve injury and aging-dependent axonal regeneration decline.

The effectiveness of an anti-CXCL13 binding molecule, e.g., an antibody or binding fragment thereof, for the promotion of axonal regeneration following peripheral nerve injury can be shown using animal models. For example, the effectiveness of an anti-CXCL13 binding molecule, e.g., an antibody or antigen-binding fragment thereof, of the disclosure for the treatment of peripheral nerve injury can be shown using an animal model for sciatic nerve injury, e.g., mice subjected to sciatic nerve "crush" as described herein below and treated with an anti-CXCL13 binding molecule of the disclosure. Animal models for other peripheral nerve injuries, such as brachial plexus injuries, spinal accessory nerve injuries, and peroneal nerve injuries are also known to those of skill in the art.

In accordance with the methods of the present disclosure, at least one anti-CXCL13 binding molecule, e.g., an antibody or antigen-binding fragment thereof, as defined elsewhere herein is used to promote a positive therapeutic response with respect to a peripheral nerve injury or damage. By "positive therapeutic response" with respect to peripheral nerve injury is intended an improvement in the injured tissue in association with nerve regeneration and/or an improvement in the symptoms associated with the injury. That is, a regenerative effect, a reversal of aging-dependent regenerative decline, epidermal reinnervation, recovery of neurological function of the injured nerve, and/or a decrease in one or more symptoms associated with the nerve injury such as the reduction of associated pain, muscle weakness, tingling, loss of feeling, and the like can be observed. Thus, for example, an improvement in the injured tissue can be characterized as a complete response. By "complete response" is intended a recovery of neurological function and absence of any associated pain, tingling, or other side effects of the injury. Alternatively, an improvement in the injury can be categorized as being a partial response. By "partial response" is intended a decrease in associated pain, some epidermal innervation and nerve regeneration, improved muscle strength, and at least partial recovery of neurological function.

In one embodiment, the anti-CXCL13 binding molecule, e.g., an antibody or antigen binding fragment, of the disclosure is used to treat sciatic nerve injury or damage. The sciatic nerve is located on the back of the leg and provides sensation on the thighs, the lower leg and the soles of the feet. Because the sciatic nerve is connected to and supplies the muscles on the knee and lower leg, extreme damage to the nerve can cause weakness in the knees, difficulty bending the knee, difficulty in bending the foot, and/or weakness in foot movements. It can also cause problems with reflexes, and the knee or leg may not respond properly when touched. Patients may experience extreme pain or tingling as a result of sciatic nerve damage.

Sciatic nerve damage can be caused by a number of factors including an injury (such as a pelvic fracture or other pelvic injury); a slipped disk; degenerative disk disease; spinal stenosis; or tumors. With damage to the sciatic nerve the patient may experience aches, tingling or burning in one or both legs. Pain may be local to one leg or to one side of the leg, hip, calf or soles of the feet, or pain may exist in both legs. When the damage to the sciatic nerve is extreme, patients may be unable to move their legs. When the nerve is damaged, pain may begin slowly and progressively worsen.

"Sciatica" is a term used to refer to the symptoms that occur when the sciatic nerve is damaged. It is not a separate medical condition but is a general term for the numbness, pain, tingling or weakness experienced in one or both legs by patients who experience damage to the sciatic nerve.

Neutralization of CXCL13 using an anti-CXCL13 monoclonal antibody or antigen binding fragment thereof of the disclosure, e.g., MAb 5261 or Mab 5378, can reduce the severity of sciatica through several different mechanisms, e.g., blockade of CXCL13 interaction with its receptor or blocking homing of CXCR5+CD8+ T cells into the DRG of the sciatic nerve.

In one embodiment, the anti-CXCL13 binding molecule, e.g., an antibody or antigen binding fragment, of the disclosure is used to treat a physical injury to a spinal accessory nerve in a subject with aging-dependent regenerative decline. Injury to the spinal accessory nerve can result in dull and achy pain in the shoulder, increasing pain upon movement, numbness in the region of the deltoid muscle, difficulty in moving the affected arm, wasting of the deltoid muscle in prolonged injuries, and weakness in the affected shoulder.

Neutralization of CXCL13 using an anti-CXCL13 monoclonal antibody or antigen binding fragment thereof of the disclosure, e.g., MAb 5378 or MAb 5261, can reduce the severity of spinal accessory nerve injury or to regenerate the damaged nerve tissue through one or more mechanisms described herein, e.g., blockade of CXCL13 interaction with its receptor or blocking homing of CXCR5+CD8+ T cells into the DRG of the spinal accessory nerve.

In one embodiment, the anti-CXCL13 binding molecule, e.g., an antibody or antigen binding fragment, of the disclosure is used to treat a brachial plexus injury in a subject with aging-dependent regenerative decline, e.g., to regenerate the damaged nerve tissue of the brachial plexus through one or more mechanisms described herein, e.g., blockade of CXCL13 interaction with its receptor or blocking homing of CXCR5+CD8+ T cells into the DRG of the brachial plexus nerve network. The brachial plexus nerves originate in the fifth, sixth, seventh and eighth cervical (C5-C8), and first thoracic (T1) spinal nerves, and innervate the muscles and skin of the chest, shoulder, arm and hand. A brachial plexus injury is the most severe nerve injury of the extremities. Based on the location of the nerve damage, brachial plexus injuries can affect part of or the entire arm. For example, an musculocutaneous nerve damage weakens elbow flexors, median nerve damage causes proximal forearm pain, and paralysis of the ulnar nerve causes weak grip and finger numbness. (Lorei, Matthew P.; Hershman, Elliott B. (1993). "Peripheral Nerve Injuries in Athletes". Sports Medicine. 16 (2): 130-47). In some cases, these injuries limit use of these limbs and cause pain. Injuries often cause weakness in the arm, diminished reflexes, and corresponding sensory deficits.

Neutralization of CXCL13 using an anti-CXCL13 monoclonal antibody or antigen binding fragment thereof of the disclosure, e.g., MAb 5378 or MAb 5261, can reverse the regenerative decline in subjects with a brachial plexus nerve injury, thereby regenerating the injured nerve tissue and reducing the severity of or eliminating the associated pain and muscle weakness, through several different mechanisms, e.g., blockade of CXCL13 interaction with its receptor or blocking homing of CXCR5+CD8+ T cells into the DRG of the brachial plexus nerve.

In another embodiment, the anti-CXCL13 binding molecule, e.g., an antibody or antigen binding fragment, of the disclosure is used to treat a peroneal nerve injury in a subject with aging-dependent regenerative decline, e.g., to regenerate the damaged nerve tissue of the peroneal nerve through one or more mechanisms described herein, e.g., blockade of CXCL13 interaction with its receptor or blocking homing of CXCR5+CD8+ T cells into the DRG of the peroneal nerve. A peroneal nerve injury, also known as peroneal neuropathy, can result in numbness or tingling in the front and or side of the lower leg, decreased sensitivity to the injured and surrounding areas, weakness in lifting the foot upwards and turning it outwards, an inability to lift the foot enough to clear the floor when walking (drop foot), or cause a slapping gait.

Clinical response to the treatments described herein can be assessed using screening techniques such as magnetic resonance imaging (MRI) scan, MRI neurography, electrodiagnostic tests, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-CXCL13 binding molecule, e.g., an antibody or antigen-binding fragment thereof, can experience the beneficial effect of an improvement in the symptoms associated with the injury.

A further embodiment of the disclosure is the use of an anti-CXCL13 binding molecule, e.g., antibodies or antigen binding fragments thereof, for diagnostic monitoring of protein levels in tissue as part of a clinical testing procedure, e.g., to determine whether a subject can benefit from the treatment described herein or determine the efficacy of a given treatment regimen. For example, detection of CXCL13 level in a subject, e.g., in or tissue in the vicinity of a specific DRG can be facilitated by coupling the anti-CXCL13 antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, 0-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

VI. Pharmaceutical Compositions and Administration Methods

Methods of preparing and administering the anti-CXCL13 binding molecule, e.g., antibodies, or antigen-binding fragments, variants, or derivatives thereof, of the disclosure to a subject in need thereof are well known to or are readily determined by those skilled in the art. The route of administration of the anti-CXCL13 binding molecule, e.g., antibody, or antigen-binding fragment, variant, or derivative thereof, can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the disclosure, an example of a form for administration would be a solution for injection, in particular for intravenous, intraperitoneal, or intraarterial injection or drip. Usually, a suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, anti-CXCL13 binding molecules, e.g., antibodies, or antigen-binding fragments, variants, or derivatives thereof, of the disclosure can be delivered directly to the site of the peripheral nerve injury thereby increasing the exposure of the injured tissue to the therapeutic agent.

As discussed herein, anti-CXCL13 binding molecules, e.g., antibodies, or antigen-binding fragments, variants, or derivatives thereof, of the disclosure can be administered in a pharmaceutically effective amount for the in vivo treatment of peripheral nervous system (PNS)damage, such as an injured peripheral nerve, e.g., an injured sciatic nerve. In this regard, it will be appreciated that the disclosed binding molecules of the disclosure will be formulated so as to facilitate administration and promote stability of the active agent. In certain embodiments, pharmaceutical compositions in accordance with the present disclosure comprise a pharmaceutically acceptable, non-toxic, sterile carrier such as physiological saline, non-toxic buffers, preservatives, and the like. For the purposes of the instant application, a pharmaceutically effective amount of an anti-CXCL13 binding molecule, e.g., an antibody, or antigen-binding fragment, variant, or derivative thereof, conjugated or unconjugated, shall be held to mean an amount sufficient to achieve effective binding to a target and to achieve a benefit, e.g., regeneration of the damaged nerve, innervation of the surrounding epidermis, recovery of neuronal function, and/or ameliorate symptoms of peripheral nerve injury, e.g., pain or tingling, or to detect the level of CXCL13 in a tissue.

The pharmaceutical compositions used in this disclosure comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject disclosure, pharmaceutically acceptable carriers include, but are not limited to, 0.01-0.1 M, e.g., 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and can be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. For example, a formulation can include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-CXCL13 antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation can be vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit such as those described in U.S. patent application Ser. No. 09/259,337. Such articles of manufacture can have labels or package inserts indicating that the associated compositions are useful for treating a subject suffering from, or predisposed to a particular type of peripheral nerve damage or injury.

Parenteral formulations can be a single bolus dose, an infusion or a loading bolus dose followed with one or more maintenance doses. These compositions can be administered at specific fixed or variable intervals, e.g., once a day, or on an "as needed" basis.

Certain pharmaceutical compositions used in this disclosure can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-CXCL13 binding molecule, e.g., antibody, or fragment, variant, or derivative thereof, that can be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-CXCL13 antibodies, or antigen-binding fragments, variants, or derivatives thereof of the disclosure can be administered to a human or other animal in accordance with the aforementioned methods of treatment in an amount sufficient to produce a therapeutic effect. The anti-CXCL13 antibodies, or antigen-binding fragments, variants, or derivatives thereof of the disclosure can be administered to such human or other animal in a conventional dosage form prepared by combining an antibody of the disclosure, e.g., MAb 5261 or MAb 5378, with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-CXCL13 binding molecules, e.g., antibodies, or antigen-binding fragments, variants, or derivatives thereof, of the disclosure can prove to be particularly effective.

By "therapeutically effective dose or amount" or "effective amount" is intended an amount of anti-CXCL13 binding molecule, e.g., antibody or antigen-binding fragment thereof, that when administered brings about a positive therapeutic response with respect to treatment of a patient with peripheral nerve injury to be treated.

Therapeutically effective doses of the compositions of the present disclosure, for treatment of peripheral nerve injury vary depending upon many different factors, including means of administration, target site, physiological state of the patient, whether the patient is human or an animal, other medications administered, whether treatment is prophylactic or therapeutic, age of the subject, and the level of CXCL13 detected in the subject prior to treatment. Usually, the patient is a human, but non-human mammals including transgenic mammals can also be treated. Treatment dosages can be titrated using routine methods known to those of skill in the art to optimize safety and efficacy.

The amount of at least one anti-CXCL13 binding molecule, e.g., antibody or antigen-binding fragment thereof, to be administered is readily determined by one of ordinary skill in the art without undue experimentation given the disclosure of the present disclosure. Factors influencing the mode of administration and the respective amount of at least one anti-CXCL13 binding molecule, e.g., antibody, antigen-binding fragment, variant or derivative thereof include, but are not limited to, the severity of the injury, the site of the injury, the peripheral nerve that is damaged, the history of the injury, and the age, height, weight, health, and physical condition of the individual undergoing therapy, including for example the level of CXCL13 detected in the subject. Similarly, the amount of anti-CXCL13 binding molecule, e.g., antibody, or fragment, variant, or derivative thereof, to be administered will be dependent upon the mode of administration and whether the subject will undergo a single dose or multiple doses of this agent.

The present disclosure also provides for the use of an anti-CXCL13 binding molecule, e.g., an antibody or antigen-binding fragment, variant, or derivative thereof, in the manufacture of a medicament for treating a peripheral nerve injury, including, e.g., sciatic nerve injury.

IX. Diagnostics

The disclosure further provides a method useful for diagnosis of peripheral nerve injury in a subject to determine whether the subject would benefit from treatment with an anti-CXCL13 binding molecule, e.g., whether the subject is experiencing aging-dependent nerve regenerative decline. The method involves measuring the expression level of CXCL13 protein or transcript in tissue, e.g., in or in close proximity to a DRG of an injured peripheral nerve or other cells or body fluid from an individual with or suspected of having a peripheral nerve injury, such as a sciatic nerve injury, and comparing the measured expression level with a standard CXCL13 expression level in normal tissue or body fluid of a young subject, whereby an increase in the expression level in the sample compared to the standard indicates that the subject would benefit from treatment with an anti-CXCL13 antibody as disclosed herein. In certain embodiments, the anti-CXCL13 antibodies of the disclosure or antigen-binding fragments, variants, and derivatives thereof, e.g., MAb 5261, MAb 5378, MAb 5080, MAb 1476, 3D2, or 3C9, are used in diagnosis the presence of aging-dependent nerve regenerative decline.

The anti-CXCL13 antibodies of the disclosure and antigen-binding fragments, and derivatives thereof, can be used to assay CXCL13 protein levels in a biological sample using classical immunohistological methods known to those of skill in the art (e.g., see Jalkanen, et al., J. Cell. Biol. 101:976-985 (1985); Jalkanen et al., J. Cell Biol. 105:3087-3096 (1987)). Other antibody-based methods useful for detecting CXCL13 protein expression include immunoassays, such as the enzyme linked immunosorbent assay (ELISA), immunoprecipitation, Western blotting, flow cytometry, PCR techniques, and the like. Suitable assays are described in more detail elsewhere herein.

By "assaying the expression level of CXCL13 polypeptide" is intended qualitatively or quantitatively measuring or estimating the level of CXCL13 polypeptide in a first biological sample either directly (e.g., by determining or estimating absolute protein level) or relatively (e.g., by comparing to the associated polypeptide level in a second biological sample). In one embodiment, the CXCL13 polypeptide expression level in the first biological sample is measured or estimated and compared to a standard CXCL13 polypeptide level, the standard being taken from a biological sample obtained from a young individual that does not have aging-dependent regenerative decline or being determined by averaging levels from a population of young individuals that do not have aging-dependent nerve regenerative decline. As will be appreciated in the art, once the "standard" CXCL13 polypeptide level is known, it can be used repeatedly as a standard for comparison. As used herein, the term "young individual(s)" is an arbitrary designation determined by a healthcare provider based on chronological age and other criteria, such as general health or genetics. In certain embodiments "young individuals" can be, for example, subjects of less than 40 years of age or less than 35 years of age, e.g., between 20 and 35 years of age.

By "biological sample" is intended any biological sample obtained from an individual, cell line, tissue culture, or other source of cells potentially expressing CXCL13. Methods for obtaining tissue biopsies and body fluids from mammals are well known in the art.

All of the references cited above, as well as all references cited herein, are incorporated herein by reference in their entireties.

The following examples are offered by way of illustration and not by way of limitation.

EXAMPLES

Example 1. Experimental Materials and Methods

The following materials, methods and protocols were applied in the Examples that follow.

Mice 8 to 10 week old wildtype C57/BL6J mice from were obtained from Charles River, and the aged mice (20 to 22-month-old) were supplied from either Charles River or the Jucker's laboratory, HIH, Tuebingen. OT I mice with a B57/BL6 genetic background were provided by the Botto's laboratory, Imperial College. All animal procedures were performed in accordance with the UK Animals Scientific Procedures Act (1986) and approved by the ethical committee of Imperial College London.

DRG Cell Culture

Sterile 15 mm glass coverslips in 24-well plates were coated with 0.003% Poly-L-ornithine (Sigma) diluted in $H_2O$ for 1 hour at 37° C. After 3 times washing with water, the coverslips were coated with 1 µg/ml laminin (Millipore) prepared in PBS (Invitrogen) for 3 hours at room temperature. After 2 wash steps with PBS, the wells were filled with DMEM and placed at 37° C. until cell plating. DRG were dissected and collected in Hank's balanced salt solution (HBSS) (Invitrogen) on ice. HBSS was then removed and replaced with 500 µl digest solution (5 mg/ml Dispase II (Sigma), 2.5 mg/ml Collagenase Type II (Worthington) in DMEM (Invitrogen)) for 40 minutes in a 37° C. water bath with gentle tube flick every 5 minutes. DRG were collected by centrifugation at 800 rpm for 2 minutes following digestion and washed once with warm DRG medium (DMEM/F12 (Invitrogen), 1×B27 (Invitrogen), 10% fetal bovine serum (FBS) (Sigma)). DRG were then resuspended with 1 ml warm DRG medium and broken up by pipetting with fire-polished Sigmacote (Sigma) coated glass pipette for 15 times. Un-dissociated tissue was filtered with a 100 µm cell strainer (BD Falcon) and cells were counted under bright-field microscope with a hemocytometer. After cell counting, cells were spun down, resuspended with warm DRG culture medium (DMEM/F12 (Invitrogen), 1×B27 (Invitrogen), 1% penicillin and streptomycin (Invitrogen)) and plated (4000 cells per well). The DRG cells were cultured at 37° C. in 5% $CO_2$ for 24 hours.

DRG Neurite Outgrowth Analysis

The average neurite length of cultured DRG cells was measured by using Neurolucida software (MBF Bioscience) with at least 100 cells (five field per coverslip randomly selected) per condition in technical and biological triplicate.

Immunocytochemistry

Cultured DRG cells were fixed with ice-cold 4% paraformaldehyde (PFA) (Sigma) in 1×PBS for 30 minutes on ice and washed with 1×PBS 3 times. Cells were blocked in 1×PBS, 0.1% Triton X, 5% normal goat serum (Abcam) at room temperature for 1 hour followed by the incubation with primary antibodies in 1×PBS, 0.1% Triton X, 2% normal goat serum overnight at 4° C. Cells were then washed 3 times with 1×PBS and incubated with secondary antibodies in 1×PBS, 0.1% Triton for 2 hours at room temperature in the dark. Cells were washed 3 times with 1×PBS and incubated with 4-6-Diamidino-2-phenylindole (DAPI, Molecular Probes, 1:5000) in 1×PBS, 0.1% Triton X for 10 minutes followed by 2× wash in PBS. The coverslips with cells facing down were transferred and mounted with Antifade mounting medium (Vectashield, H-1000) on the slides.

Sciatic Nerve Crush

Sciatic nerve was crushed following the protocol previously described (Bauder and Ferguson, (2012). JoVE (Journal of Visualized Experiments), e3606). Mice were deeply anesthetized with 2% isoflurane in 1 L/min oxygen and injected with 0.1 mg/kg buprenorphine and 5 mg/kg rimadyl subcutaneously (s.c.) for analgesia. An incision across the midline was made in the skin, the sciatic nerve was exposed by opening the fascial plane and a small deeper incision between the gluteus maximus and the anterior head of the biceps femoris.

The proximal side of exposed nerve where the three fascicles are sequentially aligned was placed on the bottom jaw of a super-fine hemostatic forceps (Fine Science Tools, 13020-12) at 1.5 mm from their tip. The nerve was crushed for 30 seconds at 3 clicks of the forceps with no nerve stretch. The skin was then closed with suture clips.

Mice were administered 0.1 mg/kg buprenorphine twice per day and 5 mg/kg rimadyl daily by s.c. injection for 3 days post-operation. Sham surgery was performed to expose the nerves without injury.

RNA Preparation and Sequencing

RNA sequencing was performed using RNA from the whole sciatic DRG tissue of young or aged 24 hours after sham or sciatic nerve injury. Specifically, sciatic DRG were dissected from 1 mouse per sample and stored in RNA later stabilization solution (ThermoFisher). Tissue was homogenized with RNase free micropestle and RNA was extracted using RNeasy kit (Qiagen) following the manufacturer's protocol. On-column DNase digestion was performed with the RNase-free DNase set (Qiagen) for 15 min to remove DNA. RNA concentrations and purity were measured using Agilent 2100 Bioanalyzer (Agilent). RNA with RNA integrity number (RIN) above 7.5 was used for library preparation. Libraries were prepared at Ospedale San Raffaele (Milan) using the TruSeq mRNA Sample Preparation kit (Illumina) and sequenced using Illumina HiSeq 2500 100-cycle, pair end sequencing.

Bioinformatic Analysis

FDR (false discovery rate) corrected P-value was implemented with Benjamini-Hochberg (BH) correction. Differentially expressed (DE) genes (FDR<0.05) of three comparisons (SNI Young, Sham Old and SNI Old versus Sham Young respectively) were analyzed for Gene Ontology (GO) and KEGG pathways using DAVID v6.7 (Huang et al., Systematic and integrative analysis of large gene lists using DAVID Bioinformatics Resources. *Nature Protoc.* 2009; 4(1):44-57; Huang et al., Bioinformatics enrichment tools: paths toward the comprehensive functional analysis of large gene lists. *Nucleic Acids Res.* 2009,) with all expressed genes in the dataset as the background. The categories of GO and KEGG pathways were selected by FDR<0.01 for both up- and down-regulation. Venn diagrams were generated using Biovenn (BioVenn—a web application for the comparison and visualization of biological lists using area-proportional Venn diagrams, T. Hulsen, J. de Vlieg and W. Alkema, BMC Genomics 2008, 9 (1): 488. The differentially upregulated genes from SNI Old versus Sham Young involved in immune response collected from GO and KEGG pathways were analyzed for protein-protein network established by STRING (Szklarczyk et al., STRING vii: protein-protein association networks with increased coverage, supporting functional discovery in genome-wide experimental datasets, Nucleic Acids Res. 2019). The stringent criteria were selected using the active interaction sources of experiments and databases, and the highest confidence of the minimum required interaction score. The network was visualized by Cytoscape (Shannon et al., Cytoscape: a software environment for integrated models of biomolecular interaction networks, Genome Research 2003 November: 13(11): 2498-504).

CXCL13 ELISA Assay

Sciatic DRG dissected from 2 young or aged mice per sample 3 days after sham or sciatic nerve injury were collected and homogenized in 150 µL Assay Diluent A supplied from Mouse CXCL13 ELISA kit (ThermoFisher) with protease inhibitors (Roche). After homogenization, Triton X-100 was added to a final 1% concentration. Samples were frozen in liquid nitrogen and thawed followed by centrifugation at 10,000×g for 5 min to remove the debris. Protein concentration was quantified using BCA protein assay kit (ThermoFisher) and 100 µL cell lysate was used for the CXCL13 ELISA assay using Mouse CXCL13 ELISA kit according to the manufacturer's protocols. CXCL13 ELISA measurements were obtained by measuring absorbance on an ELISA plate reader set at 450 nm and subtracting 550 nm values to correct for optical imperfections in the microplate. CXCL13 concentration in cell lysate was calculated according to the standard curve.

Immunohistochemistry

Mice were deeply anaesthetized by ketamine/xylazine mixture (up to 80 mg/kg body weight ketamine and 10 mg/kg body weight xylazine) via intraperitoneal (i.p.) injection and transcardially perfused with 20 ml ice-cold PBS followed by 4% PFA in a flow rate of 5 ml/min. DRG, sciatic nerves or glabrous skin of hind paws were excised and post-fixed in 4% PFA for 2 hours on ice and transferred to 30% sucrose (Sigma) for 3 days prior to embedding in OCT compound (Tissue-Tek). DRG were sectioned at 10 µm, sciatic nerves at 12 µm, interdigital footpads at 30 µm perpendicularly to the skin surface with a cryostat (Leica).

Sections were treated with a blocking solution containing 10% normal goat serum or normal donkey serum (Abcam) and 0.3% Triton X-100 in PBS for 1 hour at room temperature and stained with primary antibodies at 4° C. overnight. The primary antibodies were: anti-Tuj1 (1:500, Novus, NB100-1612), anti-CXCL13 (10 µg/ml, R&D SYSTEMS, AF470), anti-neurofilament 200 (1:100, Sigma, N4142), anti-CGRP (1:200, Abcam, ab36001), Alexa Fluor 488 conjugated-GS-IB4 (1:100, ThermoFisher, 121411), anti-SCG10 (1:500, NOVUS, NBP1-49461), anti-CD8 (1:100, ThermoFisher, 14-0081-82), anti-CD3 (1:100, Abcam, ab16669), anti-CXCR5 (1:100, Abcam, ab133706), anti-CD68 (1:200, Abcam, ab125212), anti-B220 (1:100, Biolegend, 103228), anti-MHC-I (1:100, Abcam, ab15681), anti-active caspase 3 (1:200, Cell Signaling, #9664), anti-Phospho-AKT (1:200, Cell Signaling, #4060), anti-Phospho-S6 (1:200, Cell Signaling, #5364), anti-Perforin (1:100, NOVUS, NBP1-97512), anti-Granzyme B (1:100, Abcam, ab4059), anti-PGP9.5 (1:200, Proteintech, 14730-1-AP), anti-phospho-NFκB2 (1:100, Abcam, ab194919), anti-Luciferase (1:200, Fitzgerald, 70R-12141), anti-GFP (1:500, Abcam, ab13970). Sections were washed with 1×PBS for 3 times followed by secondary antibody incubation with Alexa Fluor 488 goat anti-chicken, Alexa Fluor 488 donkey anti-chicken, Alexa Fluor 488 goat anti-rat, Alexa Fluor 488 goat anti-rabbit, Alexa Fluor 568 donkey anti-goat, Alexa Fluor 568 goat anti-rabbit (1:1000, ThermoFisher) at room temperature for 2 hours. Sections were in turn stained with DAPI (Molecular Probes, 1:5000) for 15 min at room temperature and mounted with Antifade mounting medium (Vectashield, H-1000). DRG were imaged with a Nikon Eclipse TE2000 microscope using 20× magnification. Sciatic nerves (20× magnification) and epidermis (40× magnification with oil lens) were imaged with a Leica TCS SP8 confocal laser scanning microscope.

Quantification of Immunostaining

Arbitrary fluorescence intensity was measured with ImageJ software (National Institute of Health, USA) and the relative fold change was calculated by normalized fluorescence intensity versus the control group after excluding the intensity of background. The cells designated positive for the expression of cleaved caspase 3, perforin and granzyme B showed the fluorescence intensity at least two-fold above background. Longitudinal sections of sciatic nerve stained with SCG10 were analyzed for axonal regeneration. SCG10 arbitrary intensity was measured along the nerve and percentage of intensity in every 0.5 mm was quantified away from the proximal site of crush. Regeneration index was also evaluated by calculating the distance away from the proximal injury site which the intensity was reduced to 50% level. For epidermal reinnervation, the number of intra-epidermal nerve fiber (IENF) indicated by PGP9.5 staining from sagittal sections of the skin was measured per unit of volume.

Flow Cytometry

For cell characterization in vivo, young or aged naïve or sciatic nerve-injured animals were injected with 3 µg anti-CD45-APC (I3/2.3, Biolegend) intravenously (i.v.) for 3 min. Peripheral blood or DRG were collected in 10 ml PBS with 2 mM EDTA and RPMI-1640 medium (ThermoFisher) respectively following deep anesthesia. Blood cells were collected by centrifugation at 300 g for 5 minutes at RT and erythrocytes were lysed using 1×RBC lysis buffer (Biolegend). Cells were washed with PBS 3 times and filtered by 70 µm cell strainer (Corning) to remove the clumps, and resuspended by fresh FACS buffer (0.5% BSA, 2 mM EDTA in PBS) for staining. DRG were washed by 1×PBS once and dissociated with digestion buffer (0.5 mg/ml CLSPA (Worthington, #LS005273), 7.5 µg/ml DNase I (Roche, #10104159001) in RPMI-1640) at 37° C. for 30 minutes. After digestion, DRG tissues were dispersed and filtered through 70 µm cell strainer to collect the single cell suspension and washed with rinse buffer (5% FBS in RPMI-1640). After centrifugation, the pellet was resuspended with DNase solution (250 µg/ml DNase I, 1× DNase buffer (1.21 g/L Tris Base, 0.5 g/L MgCl2 and 0.073 g/L CaCl$_2$) in RPMI-1640)) at RT for 30 minutes. Cells were washed with FACS buffer for staining.

Isolated cells from the blood and DRG samples were treated with 1.0 µg TruStain FcX anti-mouse CD16/32 antibody (Biolegend) per 106 cells in 100 µl volume to block Fc receptors for 10 min on ice and stained in FACS buffer with Brilliant Stain Buffer (BD Horizon). The following anti-mouse antibodies were used against the antigens: Pacific Blue-conjugated anti-CD45 (30-F11, Biolegend, 2 µg/ml), FITC-conjugated anti-CD62L (MEL-14, Biolegend, 5 µg/ml), Brilliant Violet 605-conjugated anti-CD19 (6D5, Biolegend, 1 µg/ml), Brilliant Violet 711-conjugated anti-CD8 (53-6.7, Biolegend, 2 µg/ml), Brilliant Violet 785-conjugated anti-TCR β (H57-597, Biolegend, 2 µg/ml), APC-conjugated anti-CD4 (RM4.5, BD, 2 µg/ml), APC/CY7-conjugated anti-CD44 (IM7, Biolegend, 2 µg/ml), PE/CY7-conjugated anti-CD69 (H1.2F3, ThermoFisher, 2 µg/ml), Biotin-conjugated anti-CXCR5 (SPRCL5, ThermoFisher, 5 µg/ml), FITC-conjugated anti-CD11b (M1/70, ThermoFisher, 2.5 µg/ml), APC-conjugated anti-F4/80 (T45-2342, BD, 2 µg/ml). LIVE/DEAD Fixable Aqua Dead Cell Stain Kit (ThermoFisher) was also used to exclude the dead cells from staining. Cells were stained with the cocktail antibodies at 4° C. in the dark for 20 min and stained with 2 µg/ml PE-Streptavidin (Biolegend) at 4° C. for 20 min after washing. Fluorescence Minus One (FMO) and PE-Streptavidin staining controls were used for the gating boundaries. In order to minimize anti-CXCR5 shedding before cell acquisition, stained cells were immediately fixed with IC fixation buffer (ThermoFisher) for 20 min at RT. Cells were washed with PBS and resuspended with FACS buffer. 20 µl Precision Count Beads (Biolegend, 424902) was added to each sample before cell acquisition by flow cytometer LSR II (BD Biosciences).

Cell Depletion Experiments

To deplete CD8 T cells in vivo, 22 to 24-month old mice were i.p. injected with 200 µg InVivoMAb rat IgG2b isotype control (LTF-2, BioXcell, BE0090) or InVivoMAb anti-mouse CD8a (YTS 169.4, BioXcell, BE0117) 3 times every other day for one week prior to sciatic nerve crush injury. One extra injection was preformed after the sciatic nerve crush when the animals were fully recovered from the anesthesia. DRG and nerves were dissected 3 days after nerve injury followed by FACS, immunostaining or regeneration assays. Depletion of CD4 T cells was performed with the same regimen used for CD8 T cell depletion using InvivoMAb Anti-mouse CD4 (YTS 191, BioXcell, BE0119) and the isotype control of rat IgG2b. Depletion of B cells was performed following a strategy described previously (Keren et al., 2011). Aged mice were i.p. injected with the following antibody cocktail: 150 µg InvivoMAb Anti-mouse CD19 (1D3, BioXcell, BE0150), 150 µg InvivoMAb Anti-mouse B220 (RA3.3A1/6.1, BioXcell, BE0067), 150 µg InvivoMAb Anti-mouse CD22 (Cy34.1, BioXcell, BE0011). 48 hours later, the mice were injected with a secondary antibody InvivoMAb Anti-rat Kappa (MAR18.5, BioXcell, BE0122), at a dose of 150 µg per mouse. All injections were carried out 2 times in one week prior to the sciatic nerve injury and one more time the day following injury. Control IgG of the same isotype of the antibodies used was injected using rat IgG2a (2A3, BioXcell, BE0089), polyclonal rat IgG (BioXcell, BE0094), mouse IgG1 (MOPC-21, BioXcell, BE0083) and mouse IgG2a (C1.18.4, BioXcell, BE0085).

CXCL13 Neutralization

For DRG ex vivo culture, young and aged mice were treated with 30 mg/kg control IgG or anti-CXCL13 antibody i.p. 3 times in one week before DRG dissection and primary cell culture (anti-CXCL13 monoclonal antibody (mAb 5378-41) and control IgG2a (mAb 2510)). Isolated DRG cells were incubated at 37° C. in 5% $CO_2$ for 24 hours followed by neurite outgrowth measurement. For CXCL13 neutralization in vivo, 30 mg/kg control IgG or anti-CXCL13 antibody were i.p. injected into the young or aged mice 4 h after sciatic nerve crush and daily until sacrifice on day 3. For the chronic nerve regeneration study, 30 mg/kg control IgG or anti-CXCL13 antibody were i.p. injected 3 times per week until the animals were sacrificed starting 4 h after injury.

Behavioral Assessment

Mice with sciatic nerve crush and chronic administration of control IgG or anti-CXCL13 antibody were used for to behavioral assessments. The left side of sciatic nerve and hind paw was injured and assessed. The investigators participating in behavioral rating were blind to the groups and the treatment.

Mechanical Sensitivity Test

Mice were put on the test chamber 30 min for acclimation before starting the behavioral assessment. The mechanical sensitivity was determined by probing the plantar surface of the left hind paw with the calibrated Von Frey filaments ranging from 0.4 g to 4 g. In order to give the sensory receptors enough time to return to baseline, the interval time was at least 30 seconds between each trail. A quick hind paw withdraw was considered as a positive response. Five trails were performed for each mouse and latency values from three positive withdrawal responses were averaged. The threshold was set at the lowest level of monofilament force.

Thermal Sensitivity Test

For thermal sensitivity, the Hargreaves test was performed as described previously (Chen et al., (2014). Nature Communications 5, 5331; Hargreaves et al., (1988). Pain 32, 77-88). Briefly, mice were put on a glass floor and separated by plastic chambers. Mice were given 30 minutes for acclimation. The thermal heat stimuli (infrared radiation source, intensity=50) were carefully placed under the plantar surface of the hind paw for no more than 10 seconds. The hind paw withdrawal time was recorded automatically. Five trails were taken on each paw and the average was calculated including the longest and shortest withdrawal time.

Adhesive Removal

Small adhesive stimuli (¼" round adhesive labels) were placed on the left hind paw of the mouse, the time to make first contact with both forepaws or mouth, as well as the time to completely remove the adhesive were recorded. Daily 10-minute training per mouse was performed for one week prior to the nerve injury. Each mouse received 3 trials. All testing was performed in the animal's home cage by a blind investigator.

Statistical Analysis

Data were statistically analyzed with Graphpad Prism 8.0 (Graphpad Software Inc., La Jolla, Calif.) and expressed as mean±SEM unless otherwise stated. Statistical comparisons were analyzed using unpaired Student's t-test for two groups. Multiple groups were analyzed using one-way analysis of variance (ANOVA) with Post-hoc Tukey's correction or two-way ANOVA with the Tukey or Sidak's test. The statistical significance was considered as $p<0.05$.

Example 2. Effects of Aging on Gene Expression Following Nerve Injury: Neuronal CXCL13 is Elevated in Aged DRG The effects of aging on gene expression in dorsal root ganglia (DRG) were assessed by RNA sequencing (RNA seq) from sciatic DRG obtained from 8-10 weeks old (young) mice and 20-22 weeks old (aged) mice proceeding (sham) and following nerve injury. The sciatic nerve of X number of young and aged mice was crushed by applying pressure to the nerve with forceps. Each mouse was injured or sham treated at approximately the same point in the sciatic nerve as described above. After 24 hours, the DRG near the site of sciatic nerve injury (SNI) or sham injury were removed, RNA extracted therefrom, and sequenced. Changes in gene expression from DRG were assessed in aged sham, young and aged after SNI in comparison to the baseline expression in young sham animals. Significantly differentially expressed (DE) genes (FDR<0.05) were analyzed by Gene Ontology (GO) and KEGG for functional classification. Typically, upregulated GO classes following a SNI in young animals implicated in neurogenesis, neurotransmitters, ion transport, G-coupled signaling and signal transduction failed to be differentially enriched in aged DRG including after a SNI. (data not shown). However, the most striking findings by GO analysis were that aged DRG displayed a very significant enrichment in the adaptive immune response including in T and partially B cell signaling, both preceding and following SNI. KEGG analysis further highlighted the presence of age- and injury-associated prominent changes in the immune response and signaling as well as in cytokine/chemokine signaling. The majority of DE genes (66.6% up-regulated and 65% down-regulated) in aged DRG were aging-dependent following injury.

Given the known prominent aging-dependent regulation of the immune response, transcripts involved in the immune response were analyzed. The analysis showed that CXCL13 is by far the most prominently upregulated gene associate with aging, both preceding and following sciatic injury. The expression of CXCL13 chemokine receptor CXCR5 was also significantly enhanced in aged DRG (FIG. 1A), suggesting the presence of a CXCL13/CXCR5 signaling axis. Measurement of the expression and localization of SCG10, a neuron specific growth-associated protein, in DRG three days after sciatic nerve crush as well as the intensity of staining in proximity to the crush site showed reduction in regeneration in the aged compared to the young animals (FIGS. 1B and C). Anti-CXCL13 immunostaining showed a significant increase in CXCL13 expression in aged sciatic DRG neurons both preceding and three days following a sciatic nerve injury (FIGS. 1D and 1E and 1F).

Example 3. CD8+ T Cells Expressing the CXCL13 Receptor CXCR5 are Elevated in Aged DRG To determine whether in vivo neuronal expression of CXCL13 attracts CXCR5+ T cells, CXCL13 was overexpressed in DRG neurons by infecting sciatic nerves of young mice with AAV-GFP or AAV-CXCL13-GFP. Six weeks after infection, interferon-γ (IFN-γ) and mannitol were delivered systemically to induce MHC-I presentation and favor blood barrier permeability respectively; immediately thereafter a sciatic nerve crush was performed and CXCR5+ T cells were measured by FACS in sciatic DRG at day 3 post-injury (data not shown). Interestingly, it was found that CXCR5+ CD8+ T cells were significantly increased in CXCL13 overexpressing DRG compared to GFP control (FIGS. 2A and B).

Since CXCL13 is a chemoattractant for CXCR5 positive B and T cells, the localization and immunophenotype of CD8+ T cells within the DRG were assessed. Immunostaining showed that the number of CXCR5+CD8+ T cells was significantly higher in aged sciatic DRG compared to young (FIG. 2C) and that the frequency of CXCR5+CD8+ T cells as a percentage of total CD8+ T cells was increased in aged as compared to young DRG 3 days following a sciatic injury (FIG. 2D). These data show that aging is associated with both an enhanced neuronal expression of CXCL13 and an increased number of CXCR5+CD8+ T cells localizing within the DRG including after a sciatic nerve injury. These data demonstrate that the tissue microenvironment of the aged DRG is significantly different from the young following nerve injury.

Example 4. CD8+ T Cells are Selectively Associated with Aging-Dependent Regenerative Decline after Sciatic Nerve Injury; Neuronal MHC-1 is Induced in Aged DRG and Plays a Significant Role in Aging-Dependent Regenerative Decline Following Sciatic Nerve Injury An analysis of whether CD8 T cells impair axonal regeneration of aged sciatic DRG neurons was undertaken. CD8 T cell depletion was carried out using an anti-CD8 monoclonal antibody that was systemically injected i.p. in aged mice one week preceding a sciatic nerve crush, while control animals received normal isotype matched IgG. Analysis of SCG10 positive sciatic nerve axons showed that the anti-CD8 monoclonal antibody significantly promoted nerve regeneration (FIG. 3A-B) and that it led to a significant reduction of CD8 T cells in the DRG as shown by immunofluorescence analysis (FIG. 3C). In stark contrast, depletion of CD4 T cells by anti-CD4 monoclonal antibody or depletion of B cells by monoclonal anti-CD19/anti-B220/anti-CD22 antibodies in the same experimental injury model, did not alter the aging-dependent regenerative decline following sciatic nerve injury (not shown).

These data directly and selectively implicate CD8+ T cells in the regenerative decline following SNI in aged animals.

RNAseq data revealed an aging-dependent enrichment for major histocompatibility complex class I (MHC-I). MHC-I is expressed by antigen-presenting cells (APCs) to present antigenic peptides on the cell membrane to activate CD8 T cells after engaging with T cell receptors (TCRs) (Zinkernagel, (2002). European Journal of Immunology 32, 2385-2392). Immunostaining for MHC-I in DRG, showed an increased expression of MHC-I in aged DRG neurons preceding and following sciatic injury (FIG. 4A). However, SNI was associated with a significant increase of the percentage of DRG neurons capable of antigen presentation as suggested by the MHC-I localization on the neuronal cell surface (FIG. 4B).

The following step was to demonstrate whether MHC-I dependent peptide presentation plays a significant role in axonal regenerative decline in the aged following sciatic nerve injury. To this end, an AAV-based approach was used to express in sciatic DRG of aged mice the virally encoded peptide sequence GAr, which inhibits MHC-I antigen presentation evading CD8 T cell immune responses (Zaldumbide and Hoeben, (2008). Biotechnology Letters 32, 749-754.). GAr was linked to a reverse tetracycline transactivator (rtTA) responsive to tetracycline/doxycycline inducible expression with a luciferase reporter (FIG. 4C, D) (Burnside et al., (2018). Brain 141, 2362-2381; Hoyng et al., (2014). Gene therapy 21, 549-557; Zaldumbide et al., (2010). Biotechnology Letters 32, 749-754). Specifically, sciatic nerves were injected bilaterally with a mixture of equal amounts of AAV-luciferase and with AAV-GAr-rtTA or control AAV-rtTA for 5 weeks when doxycycline was administered i.p. for one week. Next, a sciatic nerve crush injury was performed and animals were sacrificed 3 days later. MHC-I and cleaved caspase 3 expression were significantly reduced in luciferase positive DRG neurons following AAV-GAr-rtTA compared to control AAV-rtTA (FIG. 4E). Sciatic axonal regeneration as measured by SCG10 immunostaining was significantly enhanced upon AAV-GAr-rtTA infection (FIG. 4 F, G).

Together, these data suggest that CD8+ T cells and neuronal MHC-I play significant roles in aging-dependent regenerative decline following SNI.

Example 5. CXCL13 Neutralization Reverses Aging-Dependent Regenerative Decline and Promotes Neurological Functional Recovery after Sciatic Nerve Injury Whether neutralization of CXCL13 would promote axonal regeneration, epidermal innervation and functional recovery in the aged animals was investigated using a strategy outlined in the schematic in FIG. 5A. In initial experiments, monoclonal antibody against CXCL13 or control IgG was injected intraperitoneally as described above into young or aged mice daily for three days after sciatic nerve crush injury. Axonal regeneration was measured by anti-SCG10 immunostaining as described above. Anti-CXCL13 antibody blocked aging-dependent regenerative failure and had no effect upon axon regeneration in the young (FIG. 5B-C). CXCL13 neutralization significantly reduced the number of CXCR5+T and B cells in aged DRG (FIG. 5D). In a separate experiment the long-term delivery of the anti-CXCL13 antibody on functional recovery was tested. As described above, monoclonal antibody against CXCL13 or control IgG was delivered in young or aged animals three times per week for over five weeks starting four hours after injury. Multimodal sensory assessments were performed to measure responses to mechanical stimuli by Von Frey, to touch by the tape removal test, and to thermal nociception by Hargreaves (FIG. 5A). Data analysis showed that aged mice recovered significantly more slowly compared to the young and importantly that CXCL13 neutralization induced a significantly accelerated recovery in aged mice in all of the sensory modalities investigated selectively in the aged mice (FIG. 5E-J). Whether CXCL13 neutralization led to improved epidermal innervation was measured by PGP 9.5 immunostaining from the hairless interdigital area of the hindpaw eighteen days following sciatic nerve injury in both young and aged mice after delivery of anti-CXCL13 or control IgG. It was found that CXCL13 neutralization promoted significant epidermal innervation in aged mice (FIG. 5K, L).

These data show that CXCL13 antagonism leads to functional recovery in both thermal sensitivity and mechanoception.

Together, these data show that CXCL13 neutralization promotes axonal regeneration, epidermal reinnervation and functional recovery in the aged animals.

What is claimed is:

1. A method for promoting nerve regeneration of an injured peripheral nerve in a subject with aging-dependent regenerative decline, the method comprising administering to the subject an effective amount of an antibody or antigen-binding fragment thereof that specifically binds CXCL13 and inhibits CXCL13 interaction with its receptor; wherein the antibody or antigen-binding fragment thereof comprises
   (A) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs: 26, 30, and 33, respectively;
   (B) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs:27, 30, and 33, respectively;
   (C) a VH comprising heavy chain complementarity determining region 1 (VH-CDR1), VH-CDR2, and VH-CDR3 amino acid sequences set forth as SEQ ID NOs:19, 22, and 25, respectively; and a VL comprising light chain complementarity determining region 1 (VL-CDR1), VL-CDR2, and VL-CDR3 amino acid sequences set forth as SEQ ID NOs:28, 31, and 34, respectively; or
   (D) a VH comprising heavy chain complementarity determining region 1 (VH-CDR1), VH-CDR2, and VH-CDR3 amino acid sequences set forth as SEQ ID NOs:20, 23, and 25, respectively; and a VL comprising light chain complementarity determining region 1 (VL-CDR1), VL-CDR2, and VL-CDR3 amino acid sequences set forth as SEQ ID NOs:29, 31, and 34, respectively.

2. The method of claim 1, wherein binding of the antibody or antigen-binding fragment thereof to CXCL13 inhibits CXCL13 recruitment of CXCR5+ CD8+ T cells to the dorsal root ganglion (DRG) of the injured peripheral nerve.

3. The method of claim 1, wherein the isolated antibody or antigen-binding fragment thereof is a human or humanized antibody or antigen-binding fragment.

4. The method of claim 1, wherein the VH and VL of said antibody or antigen-binding fragment thereof comprise amino acid sequences identical to VH and VL sequences selected from the group consisting of: (i) SEQ ID NO: 6 and SEQ ID NO:7, respectively; (ii) SEQ ID NO: 8 and SEQ ID NO: 9, respectively; (iii) SEQ ID NO: 10 and SEQ ID NO:11, respectively; (iv) SEQ ID NO:12 and SEQ ID NO:13, respectively; (v) SEQ ID NO:14 and SEQ ID NO:15, respectively; and (vi) SEQ ID NO:16 and SEQ ID NO:17, respectively.

5. The method of claim 1, wherein the antibody or antigen-binding fragment is selected from the group consisting monoclonal antibodies comprising the heavy chain variable region (VH) amino acid sequence SEQ ID NO: 6 and the light chain variable region (VL) amino acid sequence SEQ ID NO: 7, the VH amino acid sequence SEQ ID NO: 10 and the VL amino acid sequence SEQ ID NO: 11, the VH amino acid sequence SEQ ID NO: 14 and the VL amino acid sequence SEQ ID NO: 15, and the VH amino acid sequence SEQ ID NO: 16 and the VL amino acid sequence SEQ ID NO: 17.

6. The method of claim 1, wherein the injured peripheral nerve is selected from the group consisting of sciatic nerve, peroneal nerve, spinal accessory nerve, and brachial plexus.

7. The method of claim 6, wherein the method regenerates the injured nerve totally or partially, reinnervates epidermal tissue, results in complete or partial recovery of neurological function of the injured nerve, or a combination thereof.

8. A method for treatment of sciatic nerve injury in a subject with aging-dependent regenerative decline and a sciatic nerve injury, the method comprising administering to the subject an effective amount of an isolated antibody or antigen-binding fragment thereof which specifically binds CXCL13 and inhibits CXCL13 interaction with its receptor; wherein the antibody or antigen-binding fragment thereof comprises
- (A) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs: 26, 30, and 33, respectively;
- (B) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs:27, 30, and 33, respectively;
- (C) a VH comprising heavy chain complementarity determining region 1 (VH-CDR1), VH-CDR2, and VH-CDR3 amino acid sequences set forth as SEQ ID NOs:19, 22, and 25, respectively; and a VL comprising light chain complementarity determining region 1 (VL-CDR1), VL-CDR2, and VL-CDR3 amino acid sequences set forth as SEQ ID NOs:28, 31, and 34, respectively; or
- (D) a VH comprising heavy chain complementarity determining region 1 (VH-CDR1), VH-CDR2, and VH-CDR3 amino acid sequences set forth as SEQ ID NOs:20, 23, and 25, respectively; and a VL comprising light chain complementarity determining region 1 (VL-CDR1), VL-CDR2, and VL-CDR3 amino acid sequences set forth as SEQ ID NOs:29, 31, and 34, respectively.

9. The method of claim 8, wherein the sciatic nerve injury is the result of pressure, stretching or cutting of the sciatic nerve.

10. The method of claim 8, wherein the VH and VL of said antibody or antigen-binding fragment thereof comprise amino acid sequences identical to VH and VL sequences selected from the group consisting of: (i). SEQ ID NO: 6 and SEQ ID NO:7, respectively; (ii) SEQ ID NO: 8 and SEQ ID NO: 9, respectively; (iii) SEQ ID NO: 10 and SEQ ID NO:11, respectively; (iv) SEQ ID NO:12 and SEQ ID NO:13, respectively; (v) SEQ ID NO:14 and SEQ ID NO:15, respectively; and (vi) SEQ ID NO:16 and SEQ ID NO:17, respectively.

11. The method of claim 8, wherein the antibody or antigen-binding fragment is a human or humanized antibody or antigen-binding fragment.

12. A method for, restoring axonal regeneration of sensory neurons following peripheral nerve injury in a subject with aging dependent regenerative decline, the method comprising administering to the subject an effective amount of an isolated antibody or antigen-binding fragment thereof which specifically binds CXCL13 and inhibits CXCL13 interaction with its receptor;
wherein the antibody or antigen-binding fragment thereof comprises
- (A) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs: 26, 30, and 33, respectively;
- (B) a VH comprising heavy chain complementarity determining region 1 (VH-CDR1), VH-CDR2, and VH-CDR3 amino acid sequences set forth as SEQ ID NOs:18, 21, and 24, respectively; and a VL comprising light chain complementarity determining region 1 (VL-CDR1), VL-CDR2, and VL-CDR3 amino acid sequences set forth as SEQ ID NOs:27, 30, and 33, respectively;
- (C) a VH comprising heavy chain complementarity determining region 1 (VH-CDR1), VH-CDR2, and VH-CDR3 amino acid sequences set forth as SEQ ID NOs:19, 22, and 25, respectively; and a VL comprising light chain complementarity determining region 1 (VL-CDR1), VL-CDR2, and VL-CDR3 amino acid sequences set forth as SEQ ID NOs:28, 31, and 34, respectively; or
- (D) a VH comprising heavy chain complementarity determining region 1 (VH-CDR1), VH-CDR2, and VH-CDR3 amino acid sequences set forth as SEQ ID NOs:20, 23, and 25, respectively; and a VL comprising light chain complementarity determining region 1 (VL-CDR1), VL-CDR2, and VL-CDR3 amino acid sequences set forth as SEQ ID NOs:29, 31, and 34, respectively.

13. The method of claim 12, wherein the VH and VL of said antibody or antigen-binding fragment thereof comprise amino acid sequences identical to VH and VL sequences selected from the group consisting of: (i). SEQ ID NO: 6 and SEQ ID NO:7, respectively; (ii) SEQ ID NO: 8 and SEQ ID NO: 9, respectively; (iii) SEQ ID NO: 10 and SEQ ID NO:11, respectively; (iv) SEQ ID NO:12 and SEQ ID NO:13, respectively; (v) SEQ ID NO:14 and SEQ ID NO:15, respectively; and (vi) SEQ ID NO:16 and SEQ ID NO:17, respectively.

14. The method of claim 12, wherein the isolated antibody or antigen-binding fragment thereof is a human or humanized antibody or antigen-binding fragment.

15. The method of claim 12, wherein the subject has a peripheral nerve injury.

16. The method of claim 15, wherein the peripheral injury is a sciatic nerve injury, brachial plexus injury, spinal accessory nerve injury, or peroneal nerve injury.

17. The method of claim 16, wherein the peripheral nerve injury is a sciatic nerve injury.

* * * * *

UNITED STATES PATENT AND TRADEMARK OFFICE
CERTIFICATE OF CORRECTION

PATENT NO. : 11,702,470 B2
APPLICATION NO. : 17/341546
DATED : July 18, 2023
INVENTOR(S) : Simone Di Giovanni et al.

It is certified that error appears in the above-identified patent and that said Letters Patent is hereby corrected as shown below:

In the Specification

In Column 2, Line 63, delete "31" and insert --32--

In Column 3, Line 60, delete "31" and insert --32--

In Column 4, Line 54, delete "31" and insert --32--

In the Claims

In Column 64, Claim 1, Line 36, delete "31" and insert --32--

In Column 65, Claim 8, Line 43, delete "31" and insert --32--

In Column 66, Claim 12, Line 41, delete "31" and insert --32--

Signed and Sealed this
Twenty-second Day of October, 2024

Katherine Kelly Vidal
*Director of the United States Patent and Trademark Office*